(12) United States Patent
Fukuma et al.

(10) Patent No.: US 8,968,653 B2
(45) Date of Patent: Mar. 3, 2015

(54) SAMPLE ANALYZER

(71) Applicant: Sysmex Corporation, Kobe-shi, Hyogo (JP)

(72) Inventors: Daigo Fukuma, Kobe (JP); Takaaki Nagai, Kobe (JP); Masaharu Shibata, Kobe (JP)

(73) Assignee: Sysmex Corporation, Hyogo (JP)

( * ) Notice: Subject to any disclaimer, the term of this patent is extended or adjusted under 35 U.S.C. 154(b) by 0 days.

(21) Appl. No.: 13/672,172

(22) Filed: Nov. 8, 2012

(65) Prior Publication Data

US 2013/0065317 A1    Mar. 14, 2013

Related U.S. Application Data

(63) Continuation of application No. 12/605,850, filed on Oct. 26, 2009, now abandoned.

(30) Foreign Application Priority Data

Oct. 28, 2008 (JP) .................. 2008-276637

(51) Int. Cl.
*G01N 33/50* (2006.01)
*G01N 33/48* (2006.01)
*G01N 33/49* (2006.01)
*G01N 15/14* (2006.01)
*G01N 21/17* (2006.01)
*G01N 27/00* (2006.01)
*G01N 15/10* (2006.01)
*G01N 15/12* (2006.01)
*G01N 15/00* (2006.01)

(52) U.S. Cl.
CPC ........ *G01N 33/5094* (2013.01); *G01N 33/4915* (2013.01); *G01N 15/14* (2013.01); *G01N 2015/1037* (2013.01); *G01N 2015/1254* (2013.01); *G01N 15/12* (2013.01); *G01N 15/147* (2013.01); *G01N 2015/0084* (2013.01); *G01N 21/17* (2013.01); *G01N 27/00* (2013.01)
USPC .......... 422/63; 422/82.02; 422/82.05; 422/73

(58) Field of Classification Search
CPC .............. G01N 2015/1037; G01N 2015/0084; G01N 15/14; G01N 15/12; G01N 2015/1254; G01N 33/4915
See application file for complete search history.

(56) References Cited

U.S. PATENT DOCUMENTS

| 4,120,657 A | * | 10/1978 | Nagy et al. .................. 205/778.5 |
| 6,525,807 B1 | | 2/2003 | Morikawa et al. |
| 2007/0038406 A1 | * | 2/2007 | Uemura et al. ............... 702/127 |

* cited by examiner

*Primary Examiner* — P. Kathryn Wright
(74) *Attorney, Agent, or Firm* — Sughrue Mion, PLLC

(57) ABSTRACT

A sample analyzer comprising: a sample preparing section for preparing first and second measurement sample including reagent and sample; a first detector for detecting a predetermined component in the first measurement sample prepared by the sample preparing section; a second detector for detecting the predetermined component in the second measurement sample prepared by the sample preparing section; and a controller configured for performing operations, comprising: (a) controlling the first detector to detect the predetermined component in the first measurement sample prepared by the sample preparing section; (b) determining the reliability of the result detected by the first detector; (c) controlling the sample preparing section to prepare the second measurement sample from the same sample when the result has been determined to be unreliable; and (d) controlling the second detector to detect the predetermined component in the second measurement sample, is disclosed.

6 Claims, 20 Drawing Sheets

SAMPLE ANALYZER

CROSS REFERENCE TO RELATED APPLICATIONS

This is a continuation application of U.S. application Ser. No. 12/605,850 filed Oct. 26, 2009 which claims priority from Japanese Patent Application No. 2008-276637 filed Oct. 28, 2008. The entire disclosure of the prior applications are hereby incorporated by reference.

FIELD OF THE INVENTION

The present invention relates to a sample analyzer for analyzing predetermined components in a sample such as blood, urine and the like.

BACKGROUND

Many sample analyzers have been developed for measuring the size of predetermined component particles in a sample such as blood, urine and the like, and analyzing the state of the particle distributions. Particularly in sample analyzers for detecting the distribution states of red blood cells, white blood cells, platelets and the like, red blood cells and platelets are measured by using an electrical resistance type measuring device since platelets have a relatively small size of 1 to 4 µm compared to the size of red blood cells which are 7 to 8 µm.

However, small size red blood cells may exist. Also, collapsed red blood cells have smaller size than usual. In those cases, red blood cells and platelets can not be reliably differentiated simply by the size.

Japanese Laid-Open Patent Publication No. 2000-275163 discloses a particle analyzer which produces highly reliable measurement results by measuring platelets by using both an electrical resistance type measuring device and an optical measuring device. This particle analyzer adopts more reliable platelet number between a platelet number by the electrical resistance type measuring device and a platelet number by the optical measuring device.

In the particle analyzer disclosed in Japanese Laid-Open Patent Publication No. 2000-275163, however, two types of measurement samples allocated from the same sample must be prepared, and the measurements are performed by the electrical resistance type measuring device and the optical type measuring device using the respective measurement samples. Disadvantages thus arise relating to the cost of the reagents used in the preparations, and the simple doubling of the number of measurement processes, which make it difficult to reduce analysis costs.

SUMMARY OF THE INVENTION

The scope of the present invention is defined solely by the appended claims, and is not affected to any degree by the statements within this summary.

A first aspect of the present invention is a sample analyzer comprising: a sample preparing section for preparing first and second measurement sample including reagent and sample; a first detector for detecting a predetermined component in the first measurement sample prepared by the sample preparing section; a second detector for detecting the predetermined component in the second measurement sample prepared by the sample preparing section; and a controller configured for performing operations, comprising: (a) controlling the first detector to detect the predetermined component in the first measurement sample prepared by the sample preparing section; (b) determining the reliability of the result detected by the first detector; (c) controlling the sample preparing section to prepare the second measurement sample from the same sample when the result has been determined to be unreliable; and (d) controlling the second detector to detect the predetermined component in the second measurement sample.

A second aspect of the present invention is a sample analyzer comprising: a sample preparing section for preparing first and second measurement sample including reagent and sample; a first detector for detecting a predetermined component in the first and second measurement sample prepared by the sample preparing section; and a controller configured for performing operations, comprising: (a) controlling the first detector to detect the predetermined component in the first measurement sample prepared by the sample preparing section using a first detection condition; (b) determining the reliability of the result detected by the first detector; (c) controlling the sample preparing section to prepare the second measurement sample from the same sample when the result has been determined to be unreliable; and (d) controlling the first detector to detect the predetermined component in the second measurement sample using a second detection condition which is different from the first detection condition.

DETAILED DESCRIPTION OF THE PREFERRED EMBODIMENTS

The embodiments are described in detail below by way of example of a blood analyzer for analyzing blood used as a sample analyzer with reference to the drawings.

First Embodiment

Figure 1:
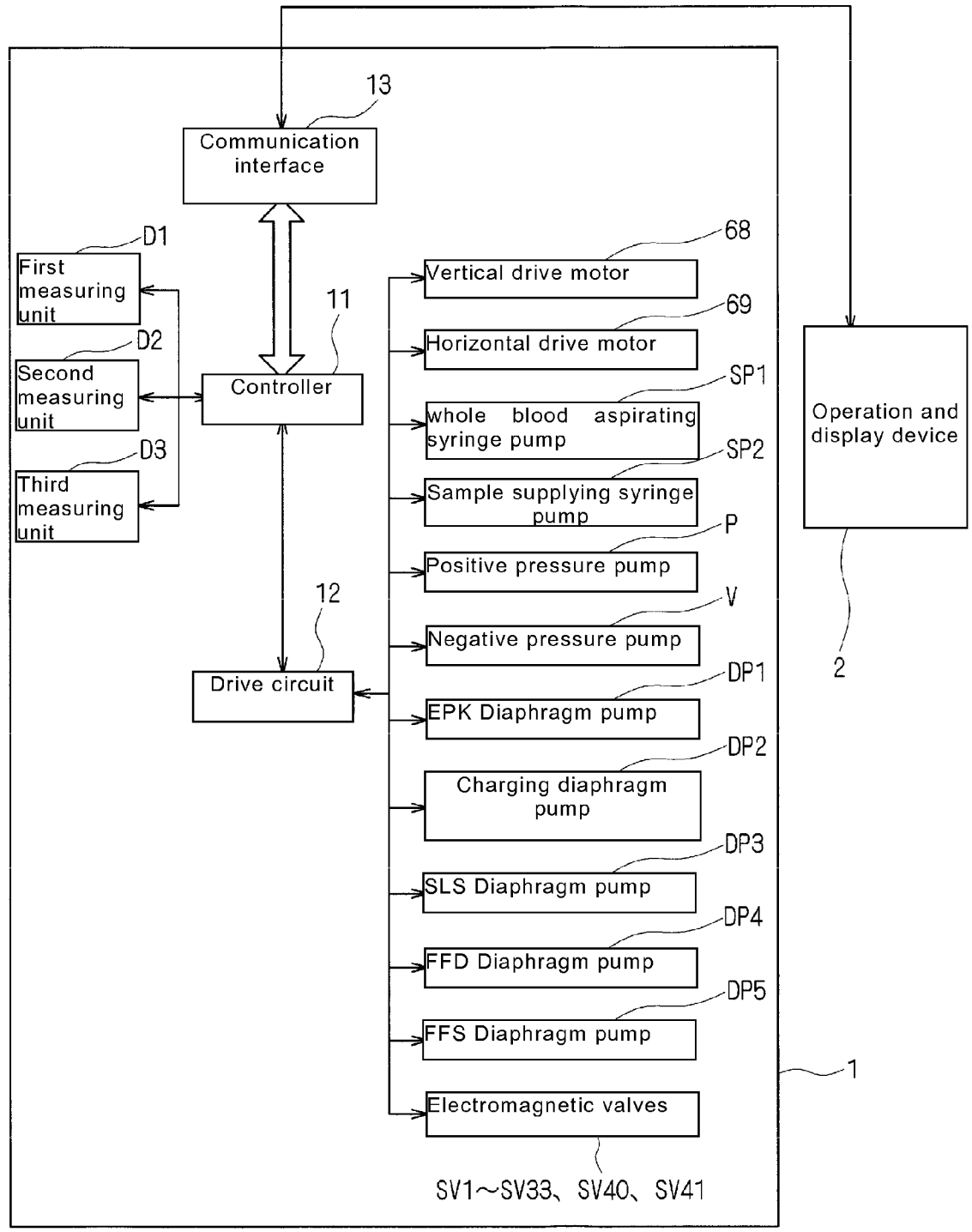
FIG. 1 is a block diagram showing the structure of a first embodiment of the sample analyzer of the present invention.

FIG. 1 is a block diagram showing the structure of a first embodiment of the sample analyzer of the present invention. The sample analyzer of the first embodiment of the present invention is configured by connecting an analyzer body 1 and an operation and display device 2 so as to be capable of data communication. The operation and display device 2 has sample analysis software installed for various types of setting related to analysis, displaying analysis results and the like; instructions are transmitted to the analyzer body 1 and measurement data are received from the analyzer body 1 via data communication between the analyzer body 1 and the operation and display device 2.

Figure 2:
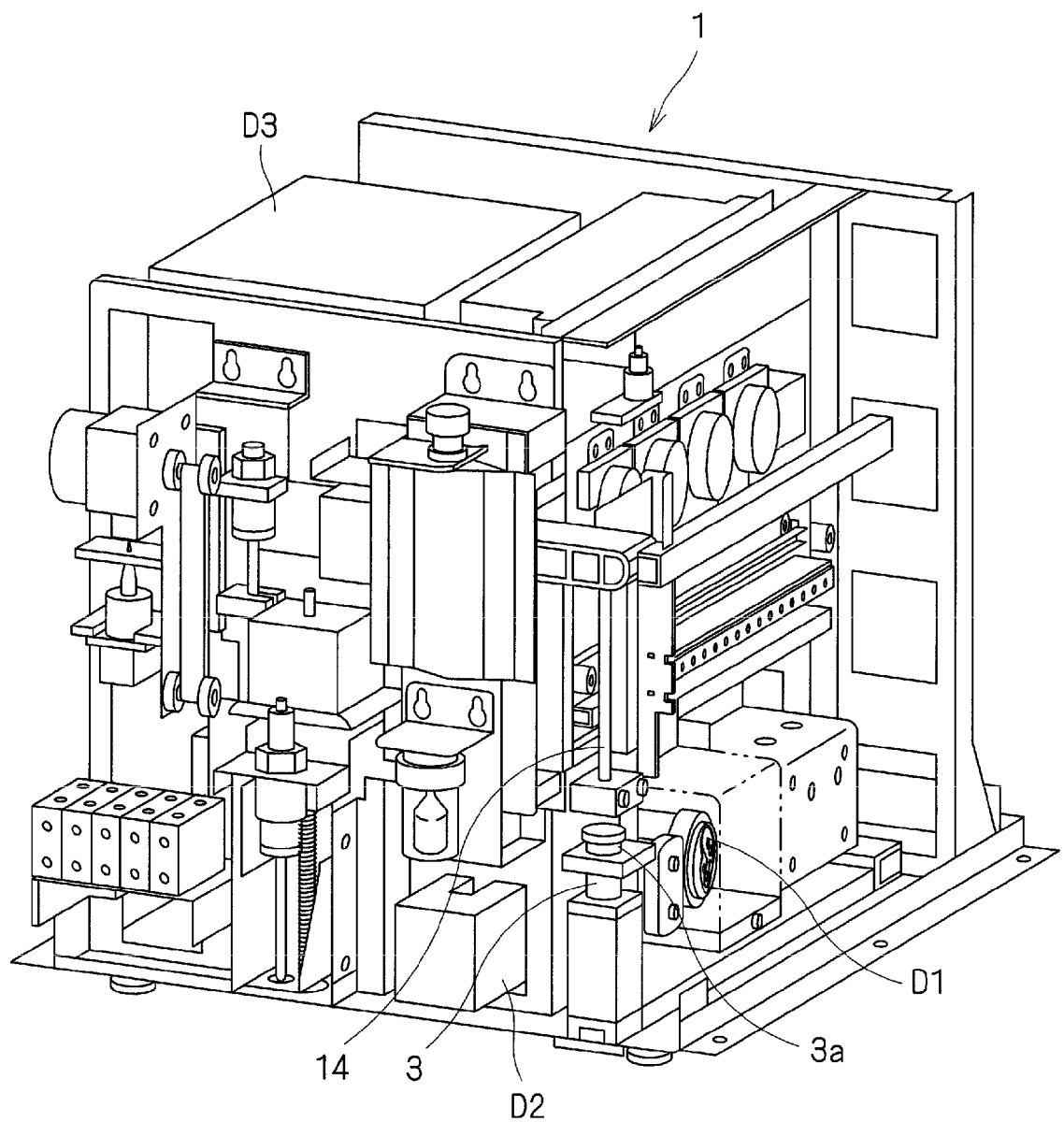
FIG. 2 is a perspective view showing the internal structure of the body of the first embodiment of the sample analyzer of the present invention.
Figure 3:
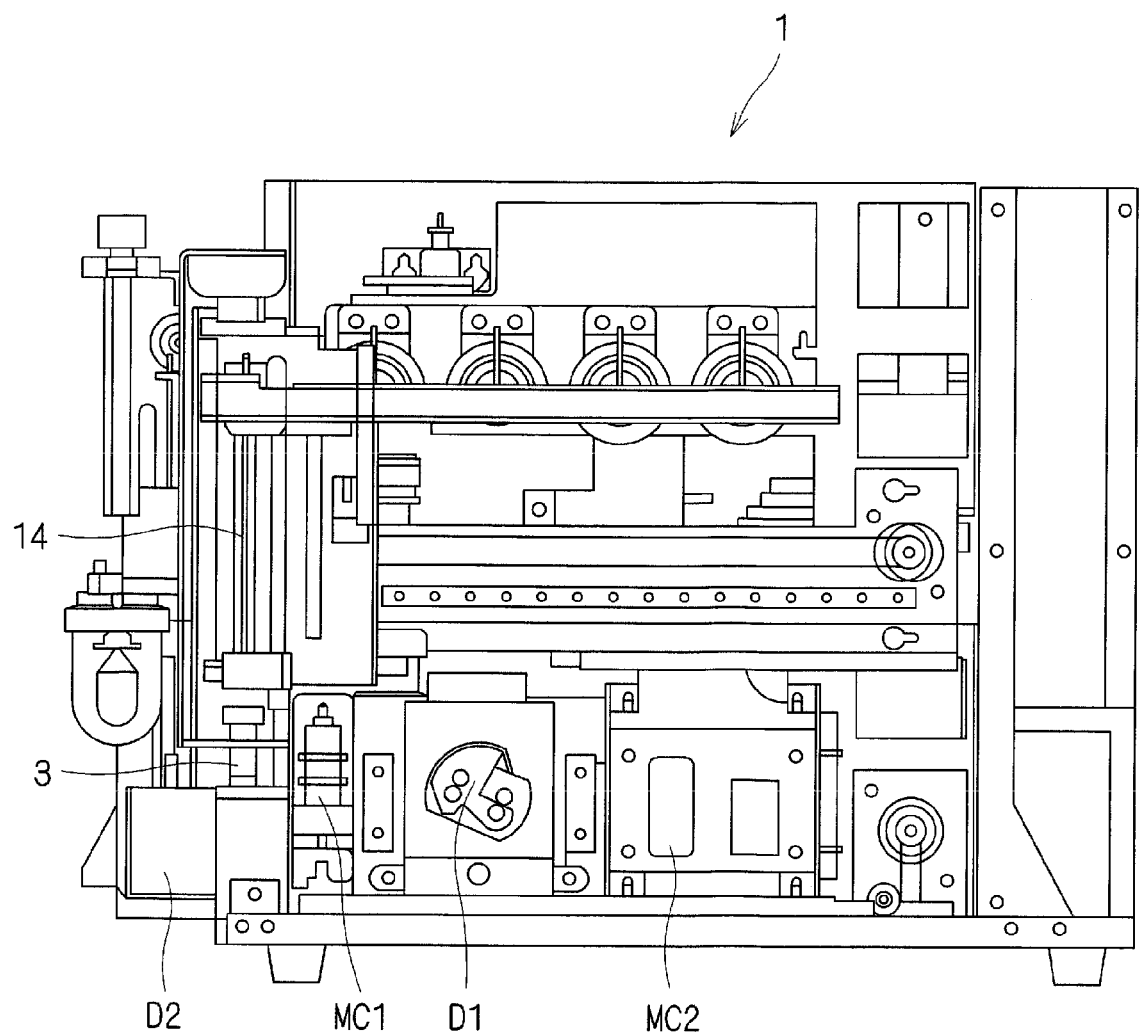
FIG. 3 is an elevation view showing the internal structure of the body of the first embodiment of the sample analyzer of the present invention.

FIG. 2 is a perspective view showing the internal structure of the analyzer body 1 of the first embodiment of the present invention, and FIG. 3 is a frontal view showing the internal structure of the analyzer body 1 of the first embodiment of the present invention. The analyzer body 1 is a blood analyzer for analyzing (measuring analyzing and the like) blood (sample) contained in a sealed container (initial container of a measurement sample) collection tube 3, and is provided with a sample placement section for placing the collection tube 3 at a predetermined position within the analyzer body 1, a sample preparing section for preparing a measurement sample by measuring and diluting the blood within the collection tube 3, and measuring units D1, D2, D3 for measuring the diluted blood.

The sample preparing section is provided with an aspirating tube (aspirator) 14 for piercing a cap 3a sealing the interior of the collection tube 3 and aspirating the sample within the collection tube 3, which is disposed at a position for preparing a sample for various analyses by aspirating a predetermined amount of blood from within the collection tube 3 and mixing reagent within a first mixing chamber (first container: HGB/RBC chamber) MC1, second mixing chamber (second container: WBC chamber) MC2, third mixing chamber (third container: RET chamber) MC3, or fourth mixing chamber (fourth container: PLT chamber) MC4, a horizontal drive section for horizontally moving the aspirating tube 14, and a vertical drive section for vertically moving the aspirating tube 14. Note that the horizontal drive section is provided with a stepping motor (horizontal drive motor) 69 as a drive source, and the vertical drive section is provided with a stepping motor (vertical drive motor) 68 as a drive source. Although the aspirating tube 14 has a flow channel extending through its interior in the longitudinal direction, and has an aspiration orifice formed near the tip for aspirating a sample or air, the present invention is not particularly limited to this arrangement.

Figure 4:
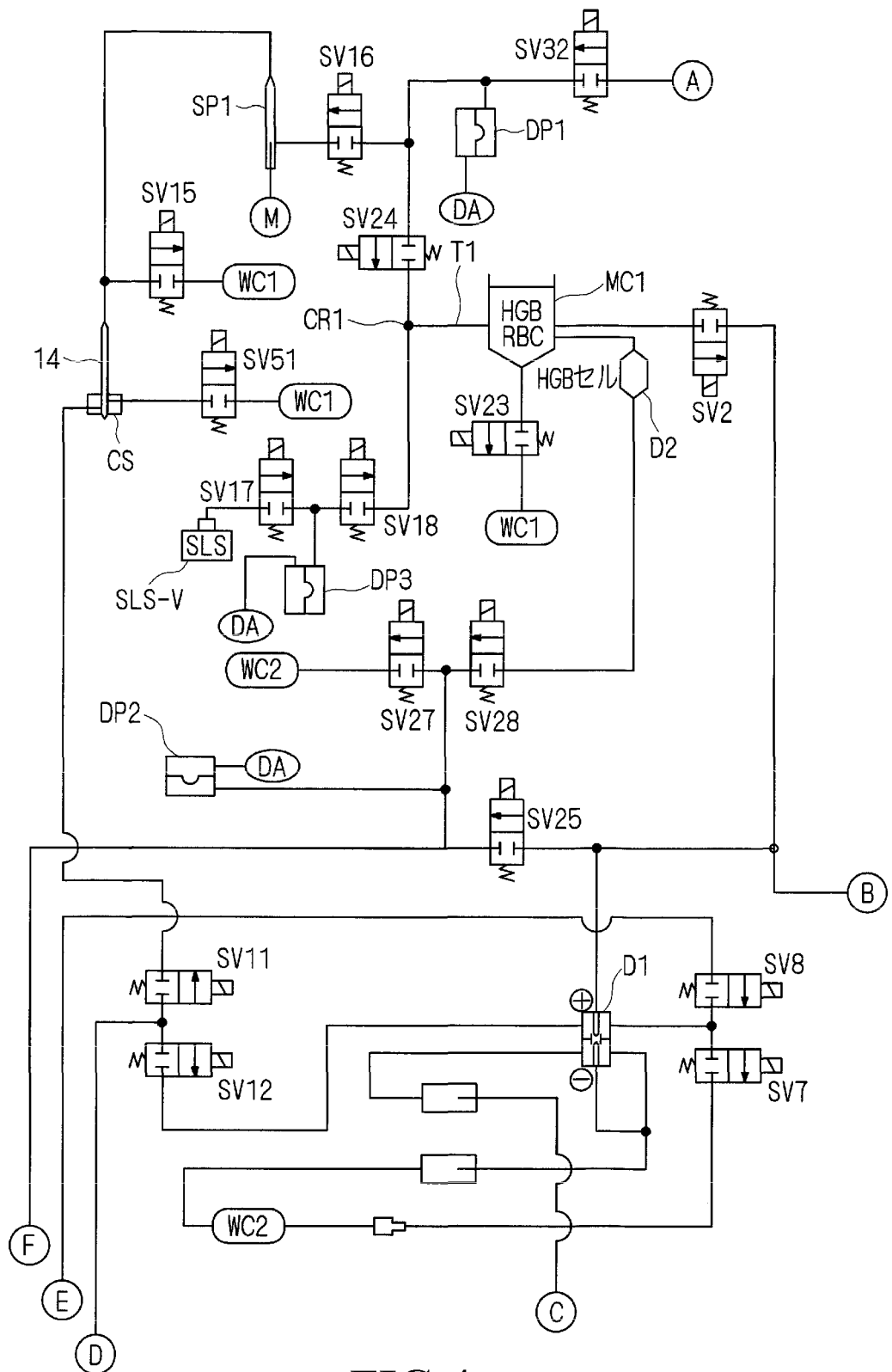
FIG. 4 is a fluid channel diagram of the sample analyzer of the first embodiment.
Figure 5:
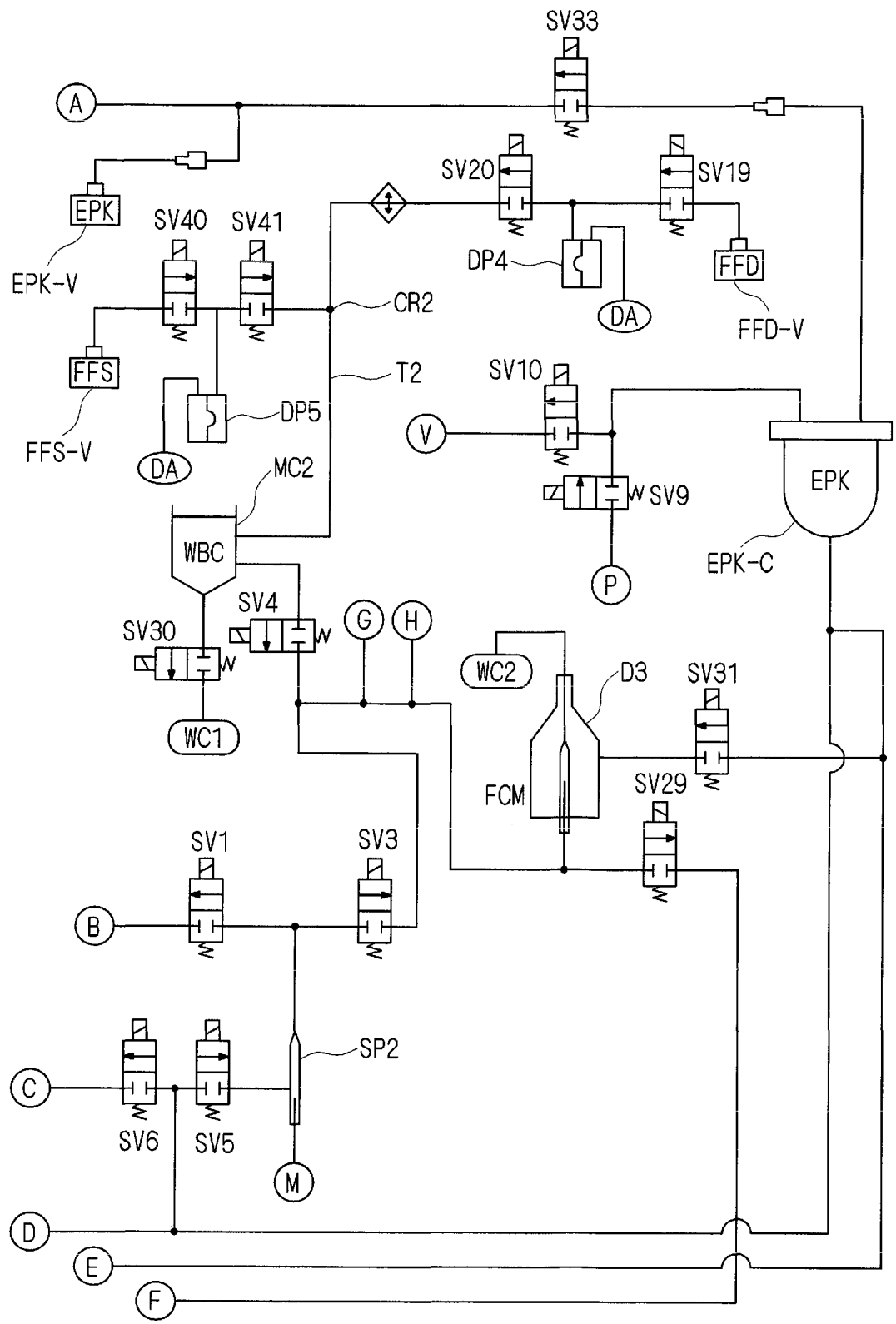
FIG. 5 is a fluid channel diagram of the sample analyzer of the first embodiment.

FIGS. 4 and 5 are fluid channel diagrams of the analyzer body 1 of the first embodiment. As shown in FIGS. 4 and 5, reagent containers accommodating a reagent are provided in the analyzer body 1 and the reagent container is connected to the fluid channel. Specifically, the reagent containers used in the first embodiment are a dilution liquid container EPK-V for accommodating dilution liquid (cleaning liquid) EPK, hemoglobin hemolytic agent container SLS-V for accommodating hemoglobin hemolytic agent SLS, white blood cell classifying hemolytic agent container (common reagent container) FFD-V for accommodating white blood cell classifying hemolytic agent FFD for dissolving red blood cells, and white blood cell classifying stain container (special reagent container) FFS-V for accommodating white blood cell classifying stain FFS.

Figure 6:
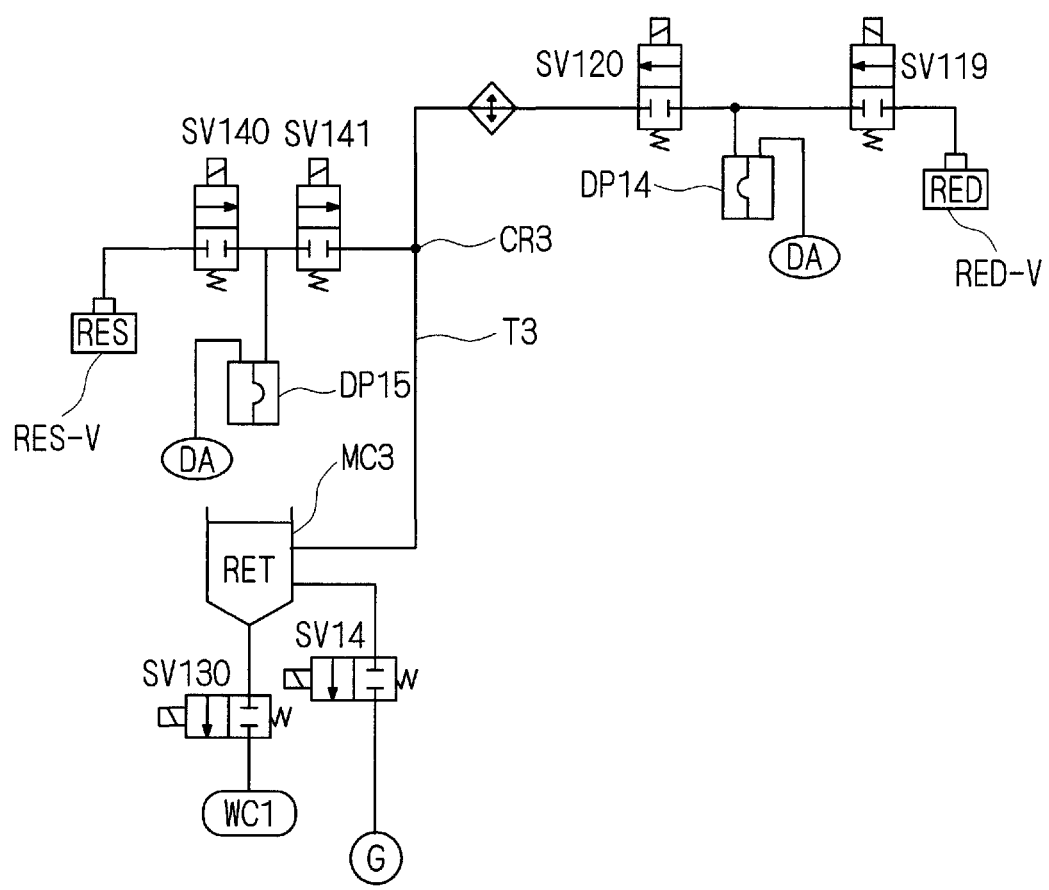
FIG. 6 is a fluid channel diagram of the sample analyzer of the first embodiment.

FIG. 6 is a fluid channel diagram provided with the RET measurement chamber MC3 of the analyzer body 1 of the first embodiment. Similar to FIGS. 4 and 5, reagent containers accommodating a reagent can be provided in the analyzer body 1 and the reagent containers may be connected to the fluid channel. The fluid channel provided with the RET measurement chamber MC3 is provided with a reticulocyte stain container RES-V for containing stain RES used to stain reticulocytes, and reticulocyte diluting liquid container RED-V for containing diluting liquid RED used for reticulocyte measurement.

Figure 7:
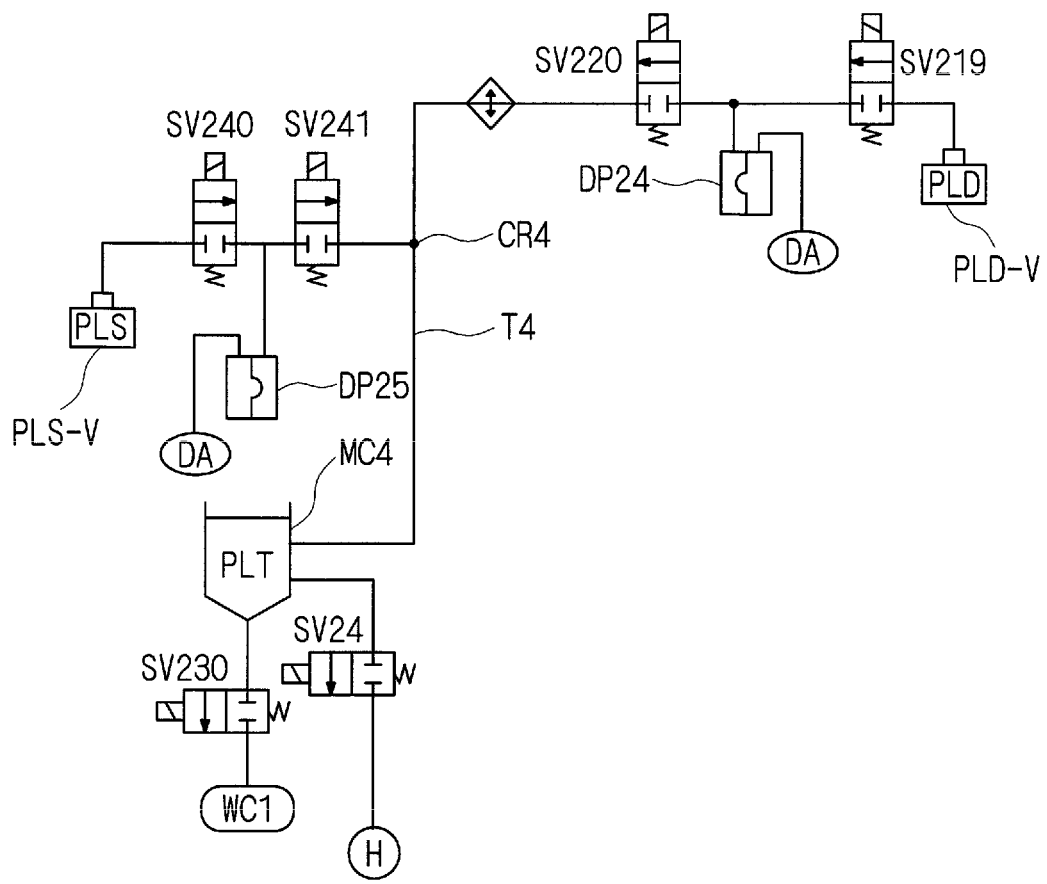
FIG. 7 is a fluid channel diagram of the sample analyzer of the first embodiment.

FIG. 7 is a fluid channel diagram provided with the PLT measurement chamber MC4 of the analyzer body 1 of the first embodiment. Similar to FIGS. 4 and 5, reagent containers accommodating a reagent can be provided in the analyzer body 1 and the reagent containers may be connected to the fluid channel. The fluid channel provided with the PLT measurement chamber MC4 is provided with a platelet stain container PLS-V for containing stain PLS used to stain platelets, and platelet diluting liquid container PLD-V for containing diluting liquid PLD used for platelet measurement. The platelet stain container PLS-V contains, for example Nile Blue as a stain.

The aspirating tube 14, whole blood aspirating syringe pump SP1, and sample supplying syringe pump SP2 are provided as a sample supplier for supplying a sample from the collection tube 3 to the first mixing chamber MC1 and/or second mixing chamber MC2. The aspirating tube 14 moves to the first mixing chamber MC1 and second mixing chamber MC2 when a predetermined amount of whole blood has been aspirated from the collection tube 3 by the whole blood aspirating syringe pump SP1 and sample supplying syringe pump SP2. Then, the predetermined amount of whole blood sample is distributed to the first mixing chamber MC1 and second mixing chamber MC2, respectively, by the whole blood aspirating syringe pump SP1 and sample supplying syringe pump SP2. Note that during RET measurement, the whole blood sample is also supplied to the third mixing chamber MC3.

Part of the whole blood sample is supplied to the fourth mixing chamber MC4 and temporarily stored. When the reliability of the sample measurement data has been determined to be low via a method which is described later, instructions are first issued to again prepare a sample and the diluting liquid PLD and stain PLS are supplied to the fourth mixing chamber MC4.

The dilution liquid container EPK-V and the hemoglobin hemolytic agent container SLS-V are connected so as to be capable of supplying reagent to the first mixing chamber MC1. That is, an EPK diaphragm pump DP1 configures the diluting liquid reagent supplying section whereby the diluting liquid can be supplied from the diluting liquid container EPK-V to the first mixing chamber MC1 by the diluting liquid supplying (EPK) diaphragm pump DP1. An SLS diaphragm pump DP3 configures the hemolytic reagent supplying section whereby the hemoglobin hemolytic agent can be supplied from the hemoglobin hemolytic agent container SLS-V to the first mixing chamber MC1 by the hemolytic agent supplying (SLS) diaphragm pump DP3.

The hemolytic agent container FFD-V and stain container FFS-V are connected so as to supply reagent to the second mixing chamber MC2. That is, the hemolytic agent can be supplied from the hemolytic agent container FFD-V to the second mixing chamber MC2 via a hemolytic agent supplying (FFD) diaphragm pump DP4; the hemolytic agent supplying (FFD) diaphragm pump DP4 configures a hemolytic agent reagent supplying section. The stain can be supplied from the stain container FFS-V to the second mixing chamber MC2 via the stain (FFS) diaphragm pump DP5; the FFS stain diaphragm pump DP5 configures a stain reagent supplying section (special reagent supplying section).

As shown in FIGS. 4 and 5, the reagent supplying channel from the dilution liquid container EPK-V to the first mixing chamber MC1 and the reagent supplying channel from the hemolytic agent container SLS-V to the first mixing chamber MC1 are joined at a midway confluence point CR1, forming a common reagent supplying channel T1 for both reagents which is connected to the first mixing chamber MC1. Although two types of reagent are supplied to the first mixing chamber MC1, there may be only a single reagent supplying orifice to the first mixing chamber MC1, thus simplifying the structure.

As shown in FIG. 5, the reagent supplying channel from the hemolytic agent container FFD-V to the second mixing chamber MC2 and the reagent supplying channel from the stain container FFS-V to the second mixing chamber MC2 are joined at a midway confluence point CR2, forming a common reagent supplying channel T2 for both reagents which is connected to the second mixing chamber MC2. Although two types of reagent are supplied to the second mixing chamber MC2, there may be only a single reagent supplying orifice to the second mixing chamber MC2, thus simplifying the structure. Note that the reagent supplying channels T1 and T2 may also be provided for each reagent. That is, two reagent supplying orifices may also be provided for each chamber MC1 and MC2.

The first measuring unit (detector, first detector) D1 performs measurements relating to red blood cells and platelets, and the second measuring unit D2 performs measurements relating to hemoglobin. The third measuring unit (other detector, second detector) D3 performs measurements relating to white blood cells. The first mixing chamber MC1 is a part for preparing a sample for analyses relating to red blood cells, platelets, and hemoglobin; the measurement sample prepared by the first mixing chamber MC1 is used in measurements performed by the first measuring unit D1 and second measuring unit D2. The second mixing chamber MC2 is a part for preparing a sample for analyses relating to white blood cells; the measurement sample prepared by the second mixing chamber MC2 is used in measurements performed by the third measuring unit D3.

The first measuring unit D1 is configured as an RBC/PLT detector for performing RBC measurements (measuring red blood cell count), and PLT measurements (measuring platelet count). The first measuring unit D1 can perform RBC and PLT measurements via a sheath flow DC detection method, and is a so-called electrical resistance measuring device.

The second measuring unit D2 is configured as an HGB detector for performing HGB measurements (measuring the amount of pigment in the blood). The second measuring unit D2 can perform HGB measurements via an SLS-hemoglobin method.

The third measuring unit D3 is configured as an optical detector capable of performing WBC measurements (white blood cell count), RET measurements (reticulocyte count), and PLT measurements (platelet count). The third measuring unit D3 performs WBC measurements, RET measurements, and PLT measurements by flow cytometry using a semiconductor laser, and is a so-called optical type measuring device.

The analyzer body 1 is provided with a controller 11 for controlling the operations of the sample preparing section, first measuring unit D1, second measuring unit D2, and third measuring unit D3. The analyzer body 1 is also provided with a drive circuit 12 for driving the electromagnetic valves SV1 through SV33, SV40, and SV41 disposed in the fluid channels configuring the sample preparing section, various types of pump motors 68, 69, SP1, SP2, P, V, DP1 through DP5 and the like; the controller 11 drives the electromagnetic valves and the like via the drive circuit 12. The controller (detector controller) 11 is capable of data communication with the operation and display device 2, so as to send and receive various types of signals and data to/from the operation and display device 2 through a communication interface 13.

Figure 8:
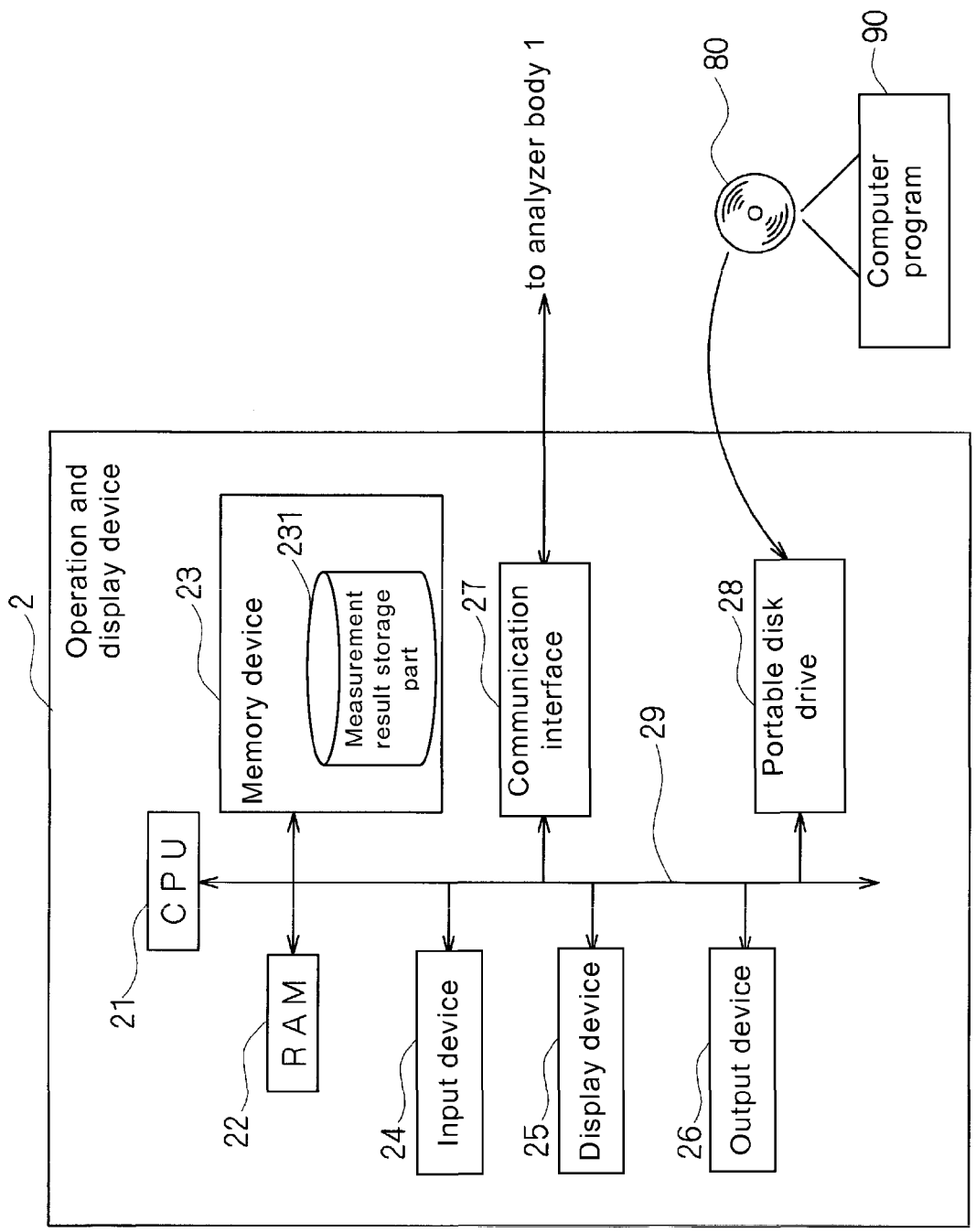
FIG. 8 is a block diagram showing the structure of a first embodiment of the operation and display device of the present invention.

FIG. 8 is a block diagram showing the structure of a first embodiment of the operation and display device of the present invention. As shown in FIG. 8, the operation and display device 2 is configured by a CPU (central processing unit) 21, RAM 22, memory device 23, input device 24, display device 25, output device 26, communication interface 27, portable disk drive 28, and an internal bus 29 connecting all the above-mentioned hardware. The CPU 21 is connected to the various hardware of the operation and display device 2 mentioned above via the internal bus 29, and controls these various hardware components and performs various software functions according to a computer program 90 stored on the memory device 23. The RAM 22 is configured by a volatile memory such as an SRAM, SDRAM or the like, and is used for developing modules during the execution of the computer program 90, and for temporarily storing data generated during the execution of the computer program 90.

The memory device 23 may be configured by a built-in fixed type memory device (hard disk), volatile memory such as an SRAM, or nonvolatile memory such as a ROM. The computer program 90 stored on the memory device 23 may be downloaded from a portable memory medium 80 such as a DVD, CD-ROM or the like which stores information such as programs and data via the portable disk drive 28, and developed from the memory device 23 to the RAM 22 during execution. Of course, the computer program 90 may also be downloaded from an external computer connected via the communication interface 27.

The memory device 23 is provided with a measurement result storage part 231 for storing the measurement results of the first measuring unit D1, second measuring unit D2, and third measuring unit D3; the CPU 21 determines the reliability of the detection results based on the stored measurement results.

The communication interface is connected to the internal bus 29, and is capable of sending and receiving data via a communication line connected to the analyzer body 1. That is, instruction information to start a measurement can be sent to the analyzer body 1 and measurement data such as measurement results and the like can be received.

The input device 24 is a data input medium such as a keyboard and mouse or the like. The display device 25 is a CRT monitor, LCD or similar display device for graphically displaying analysis results. The output device 26 is a printing device such as a laser printer, inkjet printer or the like.

The analyzer body 1 has two measurement modes relating to the measurement of platelets in the blood of a measurement sample. The first measurement mode is the CBC measurement mode in which RBC measurements and PLT measurements are performed by the first measuring unit D1, and WBC measurements art performed by the third measuring unit D3. The second measurement mode is the CBC+RET measurement mode in which RBC measurements and PLT measurements are performed by the first measuring unit D1, and the WBC measurements, RET measurements, and PLT measurements are performed by the third measuring unit D3. That is, the PLT measurements are performed by both the electrical resistance type measuring device and the optical type measuring device.

The operation of the sample analyzer is described below when the CBC measurement mode (first measurement mode) has been selected in the first embodiment. In the analyzer body 1 of the first embodiment, when the CBC measurement mode has been selected, the RBC measurement and PLT measurement is performed by the first measuring device (detector, first detector) D1 which is an electrical resistance type measuring device, and the WBC measurements are performed by the third measuring unit (other detector, second detector) D3 which is an optical type measuring device.

Figure 9:
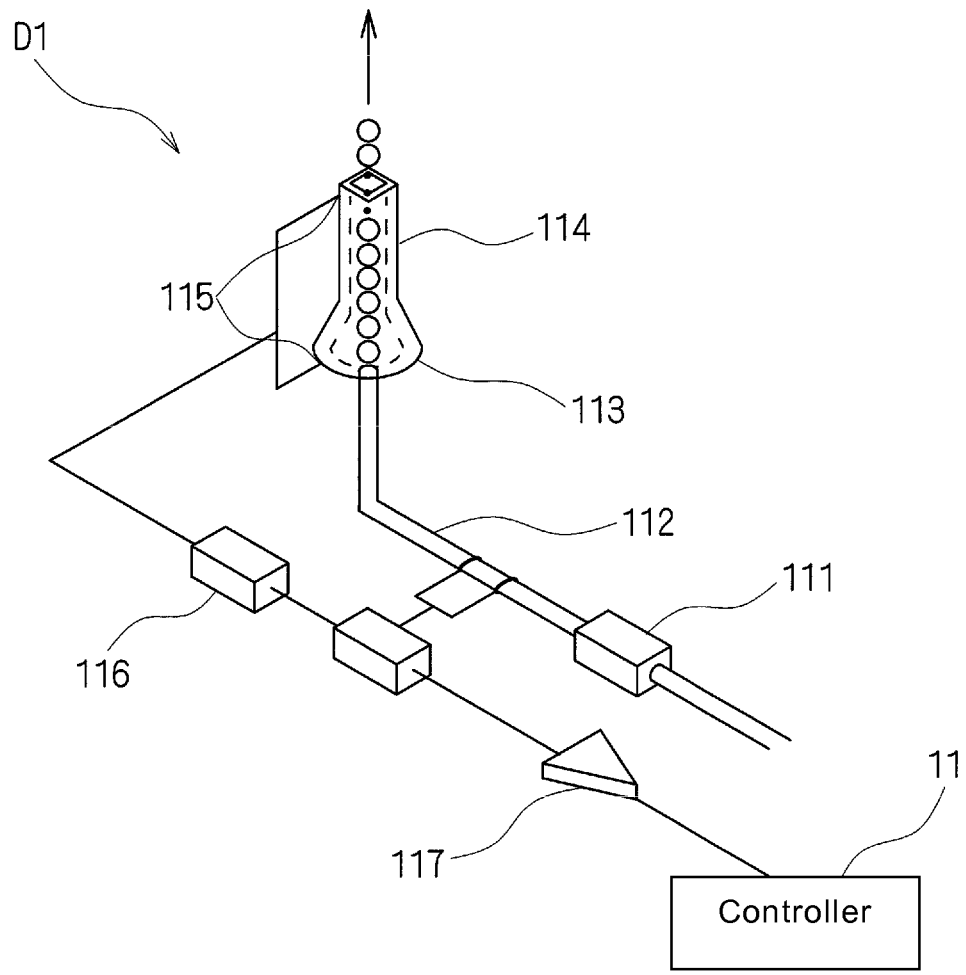
FIG. 9 is a modal view showing the main structure of a first measuring device, which is an electrical resistance type measuring device.

FIG. 9 is a modal view showing the main structure of a first measuring unit D1, which is an electrical resistance type measuring device. The first measuring unit D1 has a reactor 111; the blood sample aspirated by the aspirating tube 14, and introduced together with diluting liquid into the reactor 111.

A flow channel 112 extends from the reactor 111, and a sheath flow cell 113 is provided at the end of the flow channel 112. The measurement sample diluted in the reactor 111 is delivered to the sheath flow cell 113 through the flow channel 112. The first measuring unit D1 is provided with a sheath liquid chamber that is not shown in the drawing, so that the sheath fluid stored in the sheath fluid chamber can be supplied to the sheath flow cell 113.

In the sheath flow cell 113, a flow is formed in which the measurement sample is encapsulated by the sheath fluid. The sheath flow cell 113 is provided with an orifice 114, the flow of the measurement sample is constricted by the orifice 114 so that the particles (tangible material) contained in the measurement sample pass one by one through the orifice 114. The sheath flow cell 113 is provided with a pair of electrodes 115 which are disposed so as to have the orifice 114 interposed therebetween. A direct current (DC) power source 116 is connected to the pair of electrodes 115 to supply a DC current between the pair of electrodes 115. Then, the impedance is detected between the pair of electrodes 115 while the DC current is supplied from the DC power source 116.

The electrical resistance signals representing the change in impedance are amplified by an amp 117 and transmitted to the controller 11. The magnitude of the electrical resistance signal corresponds to the volume (size) of the particle; thus the volume of the particle can be obtained when the controller 11 performs signal processing of the electrical resistance signal.

Figure 10:
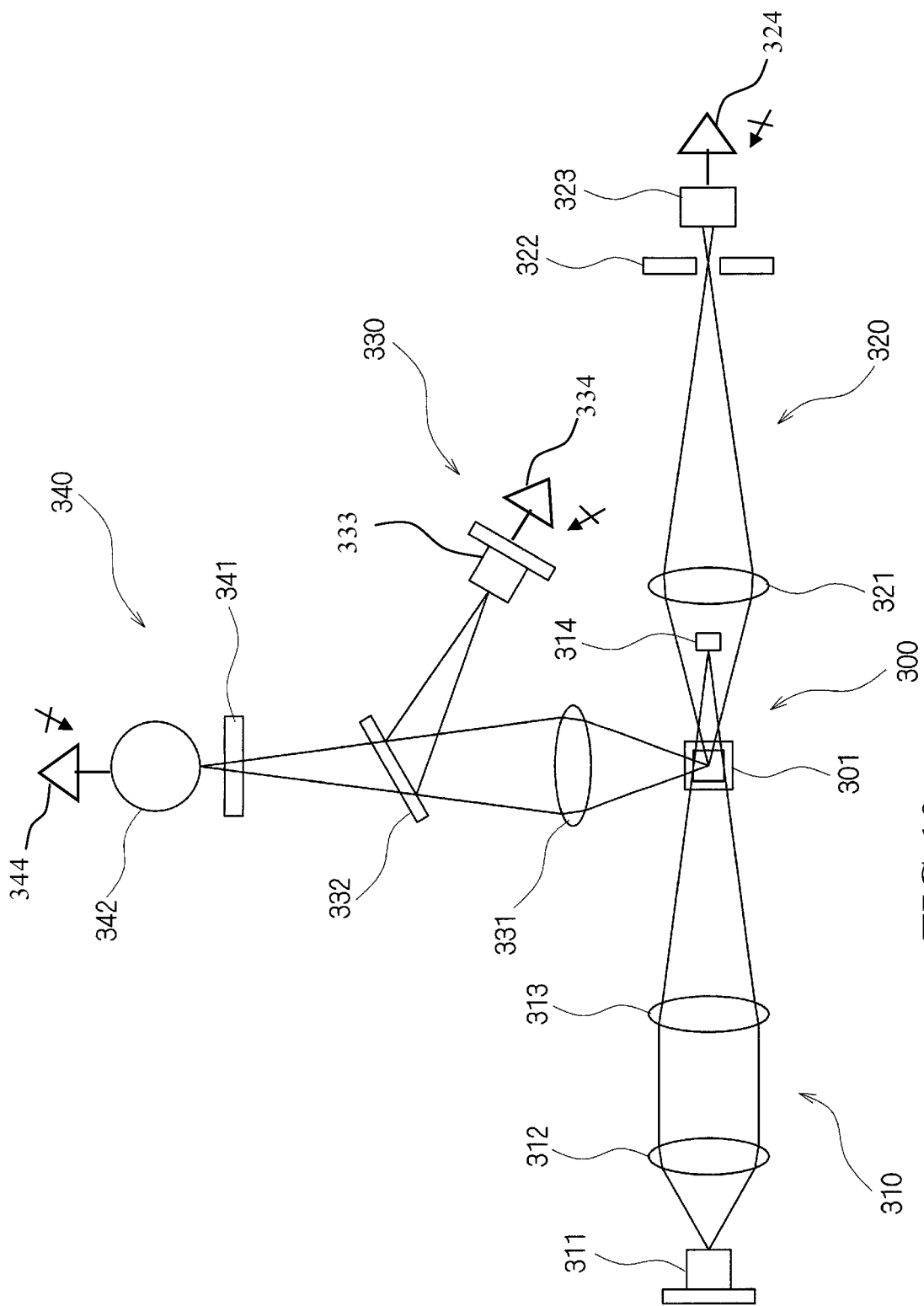
FIG. 10 is a modal view showing the main structure of a third measuring device, which is an optical type measuring device.

FIG. 10 is a modal view showing the structure of the third measuring unit D3, which is an optical type measuring device. The third measuring unit D3 receives the measurement sample at a flow cell 301, a flow is formed in the flow cell 301, the blood cells contained in the flow passing within the flow cell 301 are irradiated by a semiconductor laser light, and the blood cells are measured. The third measuring unit D3 has a sheath flow system 300, beam spot system 310, forward scattered light receiving system 320, side scattered light receiving system 330, and side fluorescent light receiving system 340.

The sheath flow system 300 forms a flow in which the blood cells contained in the measurement sample are aligned in a single row within the flow cell 301, thus improving the accuracy and reproducibility of the blood cell count. The beam spot system 310 is configured so that light emitted from the semiconductor laser 311 passes through a collimator lens 312 and condenser lens 313, and irradiates the flow cell 301. The beam spot system 310 is also provided with a beam stopper 314.

The forward scattered light receiving system 320 is configured so that the forward scattered light is collected by a forward collector lens 321, and the light passing through a pinhole 322 is received by a forward scattered light receiver (photodiode) 323, and the signal output from the forward scattered light receiver 323 according to the amount of received light is amplified by an amplifier 324. The amplification factor of the amplifier 324 is set by the CPU 21.

The side scattered light receiving system 330 is configured so that the side scattered light is collected by a side scattered light collector lens 331, and part of the light is reflected by a dichroic mirror 332, received by a side scattered light receiver (photodiode) 333, and the signal output from the side scattered light receiver 333 according to the amount of received light is amplified by an amplifier 334. The amplification factor of the amplifier 334 is set by the CPU 21.

The scattered light is a phenomenon which occurs due to the change in the direction of travel of the light caused by the presence of an obstacle in the direction in which the light is traveling, that is, a particle, such as a blood cell. Information relating to the size and material quality of the particle can be obtained by detecting the scattered light. Particularly information relating to the size of the particle (blood cell) can be obtained from the forward scattered light. Information relating to the interior of the particle, such as information concerning the material quality of the particle, can be obtained from the side scattered light.

The side fluorescent light receiving system 340 is configured so that the light passing through the dichroic mirror 332 then passes through a spectral filter 341 and is received by a fluorescent light receiver (photomultiplier) 342, and the signal output from the fluorescent light receiver 342 according to the amount of received light is amplified by an amplifier 344. The amplification factor of the amplifier 344 is set by the CPU 21.

When a fluorescent material such as a stained blood cell is irradiated with light, the fluorescent material generates light that has a longer wavelength than the irradiating light. The fluorescent intensity becomes stronger under heavy staining, so that information relating to the degree of staining of the blood cell can be obtained by measuring the intensity of the fluorescent light. Other measurements such as the classification of the blood cell can be performed via the differences in the side fluorescent light intensity.

When light is received by the light receivers 323, 333, and 342, the light receivers 323, 333, and 342 output electrical pulse signals, and measurement data are generated based on the output electrical pulse signals. The measurement data are transmitted from the analyzer body 1 to the operation and display device 2, and undergo processing and analysis in the operation and display device 2.

When the CBC measurement mode has been selected, the operation and display device 2 counts the platelets by particle size analysis of the platelets based on the measurement data of the first measuring unit D1. More specifically, the platelet count is analyzed by a histogram in which the platelet volume (units: fL) is plotted on the horizontal axis, and the number of platelets is plotted on the vertical axis.

The PLT measurement is performed by the first measuring unit D1 in the sample analyzer having the above configuration. When, for example, collapsed red blood cells contaminate the sample and the size of the particles is measured by the first measuring unit D1, the value of the red blood cells which approach the size of platelets can not be ignored and it becomes difficult to accurately count the platelets. In the sample analyzer of the first embodiment of the present invention, when the measurement data of a first PLT measurement is analyzed and it is determined that the measurement data are not reliable, the PLT measurement is then performed by the third measuring unit D3.

Figure 11:
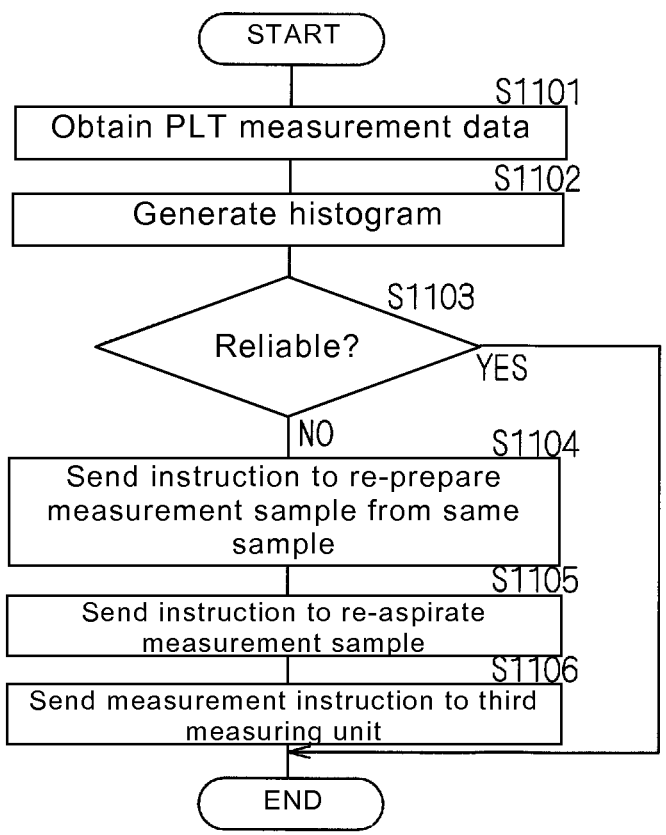
FIG. 11 is a flow chart showing the sequence of CPU processing of the operation and display device of the first embodiment of the sample analyzer of the present invention.

FIG. 11 is a flow chart showing the sequence of the processing by the CPU 21 of the operation and display device 2 of the first embodiment of the sample analyzer of the present invention. The CPU 21 of the operation and display device 2 obtains measurement data as a PLT measurement result from the controller 11 of the analyzer body 1 (step S1101).

The CPU 21 generates a histogram based on the obtained measurement data (step S1102), and displays the histogram on the display device 25. The generated histogram plots the platelet volume on the horizontal axis and the PLT count on the vertical axis.

The CPU 21 determines whether the measurement data are reliable (step S1103). The process of determining whether the PLT measurement data are reliable is not particularly limited. In the present embodiment, the measurement data are determined unreliable when the PLT count, that is, the number of platelets, is less than a predetermined value, or a platelet distribution anomaly occurs.

Figure 12:
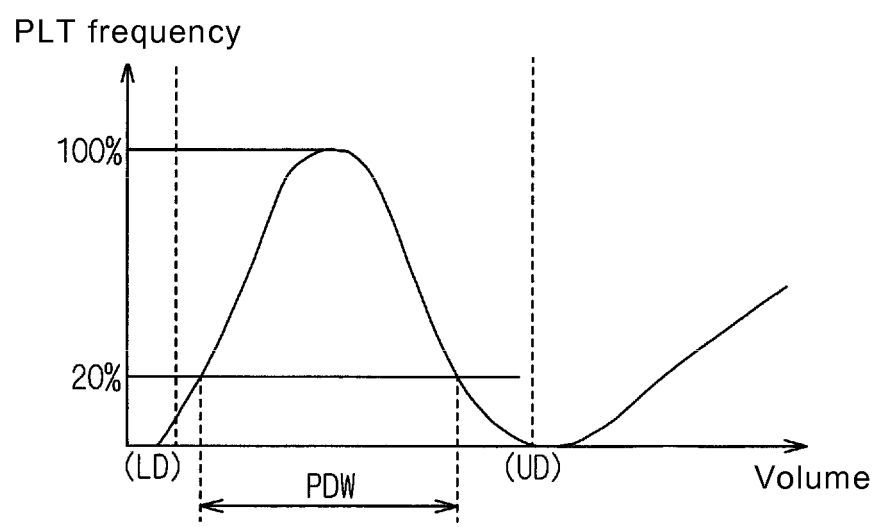
FIG. 12 shows an illustration of the reliability determination based on a histogram.

FIG. 12 shows an illustration of the reliability determination based on a histogram. The histogram of FIG. 12 shots the PLT count (count values) plotted on the vertical axis and the platelet size plotted on the horizontal axis. LD is the platelet size when a predetermined small size is as a frequency standard; UD is the platelet size when a predetermined large number is set as the frequency standard. That is, when the PLT count exceeds the LD frequency standard, the measurement data re determined to be unreliable due to the high possibility of impurities affecting the count. When the PLT count exceeds the UD frequency standard, the measurement data are determined to be unreliable due inadequate convergence when the count value is down, that is, the high possibility of impurities.

The distribution width PDW is calculated for the 20% level when the height of the peak of the PLT count is 100%, And a distribution anomaly is determined to exist when PDW is greater than a predetermined standard width.

Figure 13:
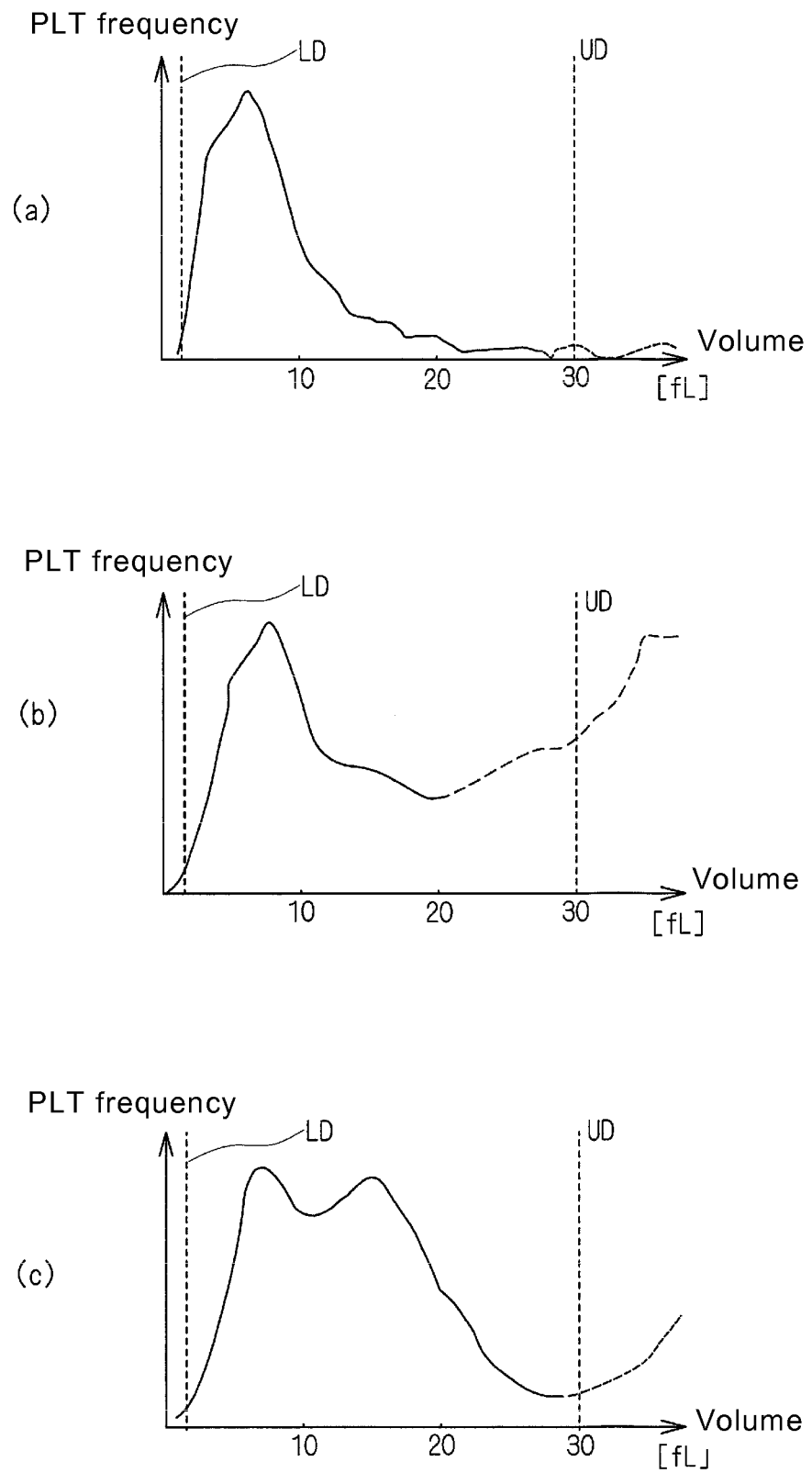
FIG. 13(a) shows an illustration of a histogram based on reliable PLT measurement data.
FIG. 13(b) shows an illustration of a histogram when the UD platelet count value exceeds the frequency standard.
FIG. 13(c) shows an illustration of a histogram when there are two or more peaks in the PLT frequency.

FIG. 13 shows an illustration of a histogram based on PLT measurement data. FIG. 13(*a*) shows a pattern example of a measurement data histogram. As shown in FIG. 13(*a*), when the measurement data are reliable, the PLT count in LD and UD are adequately smaller than the frequency standard, And the distribution width PDW is also smaller than the standard width.

FIG. 13(*b*) shows an example of a histogram when the UD platelet count value exceeds the frequency standard. In this case, the UD PLT frequency does not exceed the frequency standard, but the distribution width PDW does exceed the standard width, so a platelet distribution anomaly is determined.

FIG. 13(*c*) shows an example of a histogram when there are two or more peaks in the PLT frequency. In this case, the LD and UD PLT frequency is adequately smaller than the frequency standard, but the distribution width PDW exceeds the predetermined standard width, so a platelet distribution anomaly is determined. A distribution anomaly may also be determined when there are two or more distribution peaks even though the distribution width PDW does not exceed the predetermined standard width.

Figure 14:
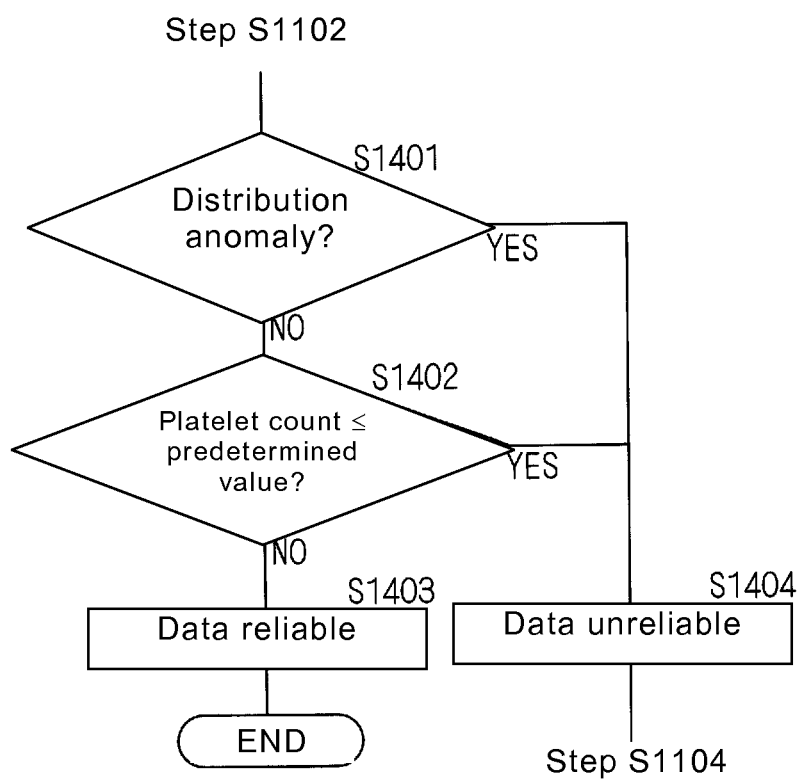
FIG. 14 is a flow chart showing the sequence of the reliability determination process of the operation and display device of the first embodiment of the sample analyzer of the present invention.

FIG. 14 is a flow chart showing the sequence of the reliability determination process of the CPU 21 of the operation and display device 2 of the first embodiment of the sample analyzer of the present invention. The CPU 21 of the operation and display device 2 generates a histogram based on the obtained measurement data (step S1102), and determines whether a platelet distribution anomaly exists (step S1401).

When the CPU 21 has determined that a platelet distribution anomaly exists (step S1401: YES), the CPU 21 then determines the data are unreliable (step S1404), and the process continues to step S1104. When the CPU 21 has determined that a platelet distribution anomaly does not exist (step S1401: NO), the CPU 21 then determines whether the platelet count value is less than a predetermined value (step S1402).

When the CPU 21 has determined that the platelet count value is less than the predetermined value (step S1402: YES), the CPU 21 then determines the data are unreliable (step S1404), and the process continues to step S1104. It is believed that an increase in small platelets may lead to platelets leaked from the count target. When the CPU 21 has determined that the platelet count value exceeds a predetermined value (step S1402: NO), the CPU 21 determines the data are reliable (step S1403) and the process ends.

Returning now to FIG. 11, when the CPU 21 of the operation and display device 2 has determined that the data are unreliable (step S1103: NO), the CPU 21 sends an instruction to again prepare a measurement sample from the same sample to the analyzer body 1 (step S1104). The controller 11 of the analyzer body 1 receives the re-preparation instruction, and issues an instruction to the drive circuit to operate the sample preparing section.

The CPU 21 sends an instruction to re-aspirate the re-prepared measurement sample to the analyzer body 1 (step S1105). The controller 11 of the analyzer body 1 receives the re-aspiration instruction, and issues an instruction to the drive circuit 12 to operate the aspirating tube 14.

The CPU 21 sends a measurement instruction to measure the re-aspirated measurement sample by the third measuring unit D3, that is to perform measurement using the optical type measuring device, to the analyzer body 1 (step S1106). The controller 11 of the analyzer body 1 receives the measurement instruction and sends a measurement start signal to the third measuring unit D3. When the CPU 21 determines that the data are reliable (step S1103: YES), the CPU 21 ends the process.

Figure 15:
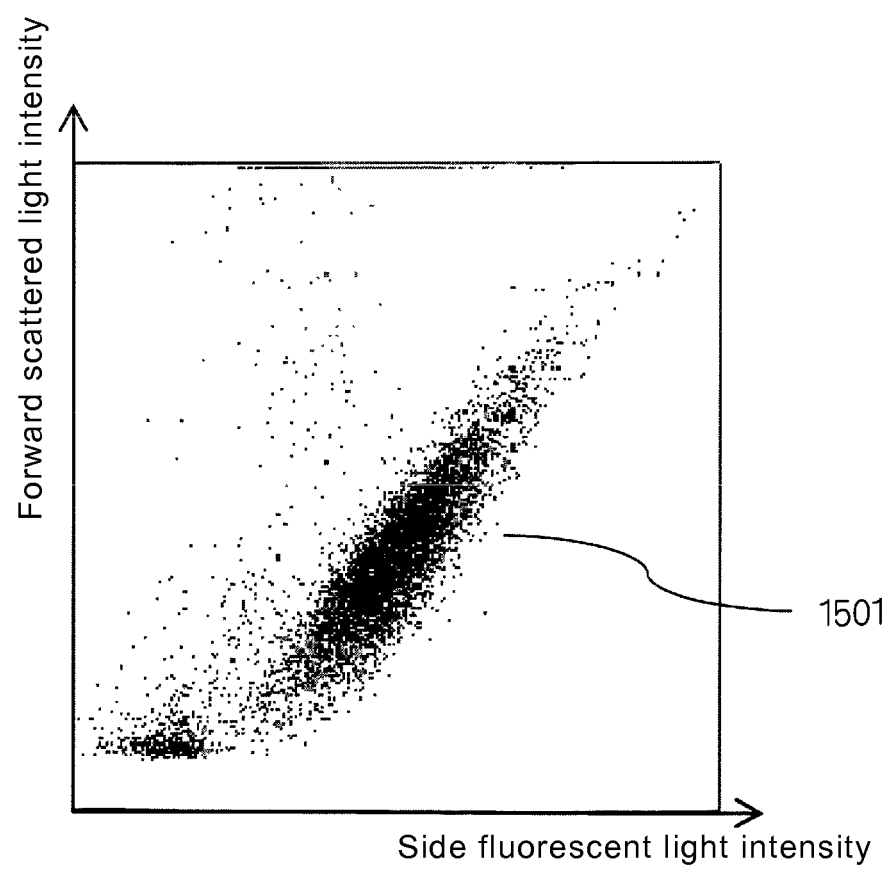
FIG. 15 shows an illustration of a scattergram representing the PLT re-measurement results of the first embodiment of the sample analyzer of the present invention.

FIG. 15 shows an illustration of a scattergram representing the PLT re-measurement results of the first embodiment of the sample analyzer of the present invention. In the scattergram of FIG. 15, the forward scattered light intensity is plotted on the vertical axis, and the side fluorescent light intensity is plotted on the horizontal axis; measurements are performed by changing the stain (for example, Nile Blue) to increase the degree of staining of the platelets. As is made clear by FIG. 15, the platelet count value is concentrated in region 1501, and there is no region in which the red blood cells and impurities intersect. Therefore, the blood can be analyzed with excellent precision by changing the detection method of the first embodiment, that is, the second detection condition according to the reliability of the first measurement data.

Since the measurement sample is re-prepared based on the same sample, and the operations of the sample preparing section and the aspirating tube 14 controlled so as to re-aspirate the prepared measurement sample only when reliable measurement data can not be obtained as the detection results of the predetermined components, the reagent used in preparing the sample is conserved, and the increase in the number of measurement processes can be limited to a minimum.

Second Embodiment

The structure of the sample analyzer of the second embodiment of the present invention is identical to that of the first embodiment with like parts designated by like reference numbers, and further detailed description is therefore omitted. The second embodiment, like the first embodiment, provides the selection of the CBC+RET measurement mode (second measurement mode), but does not provide the CBC measurement mode (first measurement mode).

The operation of the sample analyzer is described below when the CBC+RET measurement mode (second measurement mode) has been selected in the second embodiment. In the analyzer body 1 of the second embodiment, when the CBC+RET measurement mode is selected, the RBC count and PLT count are performed by the first measuring unit D1, and the WBC measurement, RET measurement, and PLT measurement are performed by the third measuring unit (detector) D3.

Since main structure of the first measuring unit D1, which is an electrical resistance type measuring device, and the structure of the third measuring unit D3, which is an optical type measuring device, are identical to those of the first embodiment, like parts are designated by like reference numbers, and further detailed description is omitted.

When the CBC+RET measurement mode (second measurement mode) has been selected, the operation and display device 2 the platelets are respectively counted by analyzing the particle size of the platelets based on the measurement data of the first measuring unit D1 and the measurement data of the third measuring unit D3. More specifically, in the case of the measurement data of the first measuring unit D1, the platelet count is analyzed by creating a histogram and plotting the platelet volume on the horizontal axis and plotting the PLT frequency on the vertical axis. In the case of the measurement data of the third measuring unit D3, the platelet count is analyzed by creating a histogram and plotting the forward scattered light intensity on the horizontal axis and plotting the PLT frequency (platelet count) on the vertical axis.

In the sample analyzer of the above configuration, the PLT measurement is performed by both the first measuring unit D1 and the third measuring unit D3. Although the size of a predetermined component of the sample is respectively measured by the first measuring unit D1 using an electrical resistance type measuring device and by the third measuring unit D3 using an optical type measuring device, the numerical value of the number of red blood cells approaching the size of platelets can not be ignored when, for example, collapsed red blood cells are included in the sample, thereby making it difficult to accurately count the number of platelets. In the sample analyzer of the second embodiment of the present invention, the reliability of the first PLT measurements performed by the first measuring unit D1 and third measuring unit D3 are respectively analyzed, and the measurement data with the higher reliability are used. When both measurement data are reliable, the measurement data of the third measuring unit D3 are used, and when both measurement data are unreliable, a second PLT measurement is performed by the third measuring unit D3.

Figure 16:
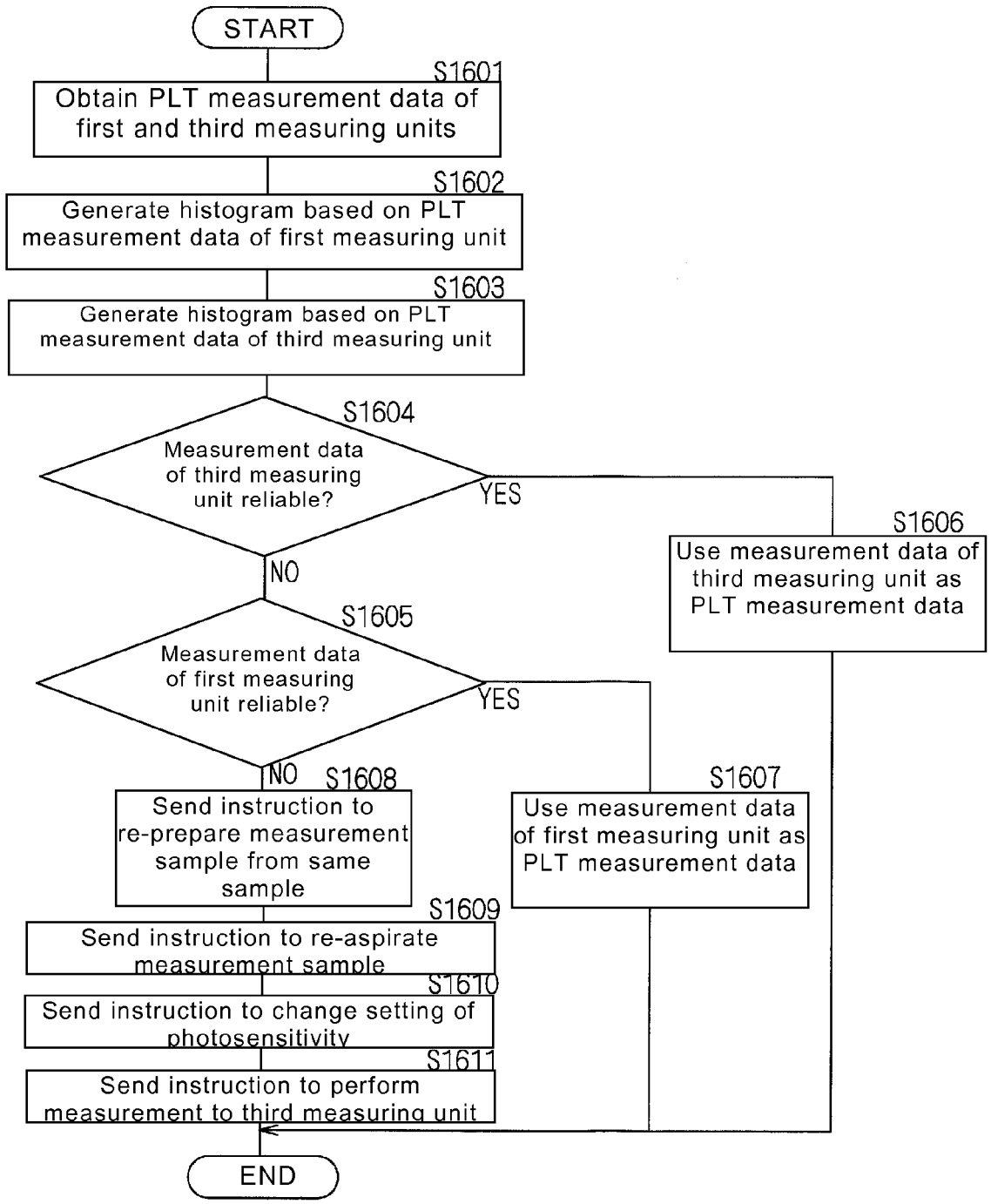
FIG. 16 is a flow chart showing the sequence of CPU processing of the operation and display device of a second embodiment of the sample analyzer of the present invention.

FIG. 16 is a flow chart showing the sequence of the processing by the CPU 21 of the operation and display device 2 of the second embodiment of the sample analyzer of the present invention. The CPU 21 of the operation and display device 2 obtains the respective measurement data of the first measuring unit D1 and the third measuring unit D3 from the controller 11 of the analyzer body 1 (step S1601). Note that in the measurement performed by the third measuring unit D3, the CPU 21 transmits a predetermined amplification factor to the amplifiers 324, 334, 342. Thus, the light receiving systems 320, 330, 340, have predetermined detection sensitivities.

The CPU 21 generates a histogram based on the obtained measurement data of the first measuring unit D1 (step S1602), and displays the histogram on the display device 25. The generated histogram plots the platelet particle size on the horizontal axis and the PLT count on the vertical axis.

The CPU 21 generates a histogram based on the obtained measurement data of the third measuring unit D3 (step S1603), and displays the histogram on the display device 25. The generated histogram plots the side fluorescent light intensity on the horizontal axis, and plots the forward scattered light intensity on the vertical axis.

The CPU 21 determines whether the measurement data of the third measuring unit D3 are reliable (step S1604). The process of determining whether the PLT measurement data are reliable is not particularly limited. In the second embodiment, similar to the first embodiment, the measurement data are determined unreliable when the PLT count, that is, the number of platelets, is less than a predetermined value, or a platelet distribution anomaly occurs.

Figure 17:
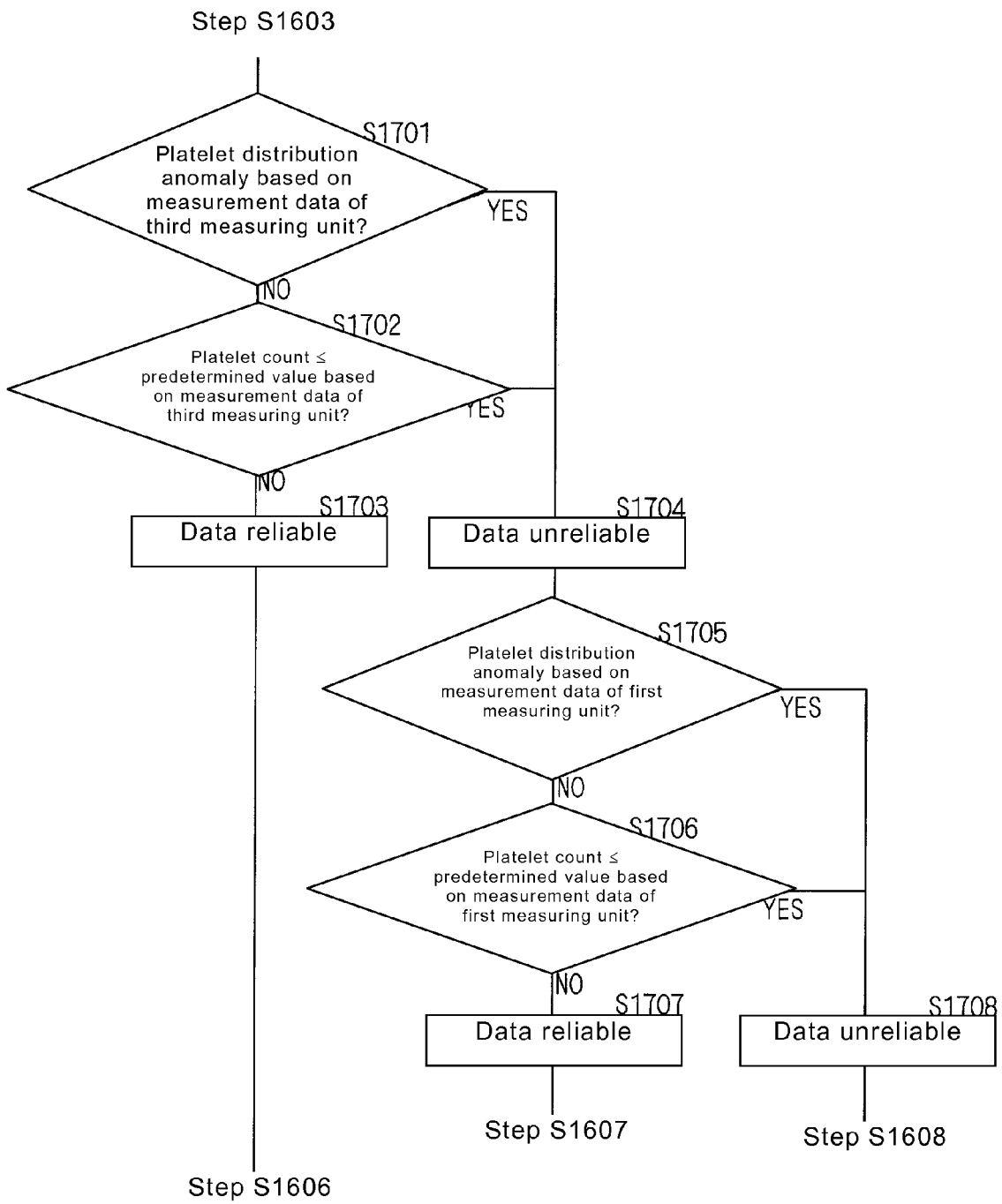
FIG. 17 is a flow chart showing the sequence of the reliability determination process of the operation and display device of the second embodiment of the sample analyzer of the present invention.

FIG. 17 is a flow chart showing the sequence of the reliability determination process of the CPU 21 of the operation and display device 2 of the second embodiment of the sample analyzer of the present invention. The CPU 21 of the operation and display device 2 generates a histogram based on the obtained measurement data of the first measuring unit D1 (step S1602), and generates a scattergram based on the obtained measurement data of the third measuring unit D3 (step S1603), then determines whether a platelet distribution anomaly exists based on the measurement data of the third measuring unit D3 (step S1701).

Figure 18:
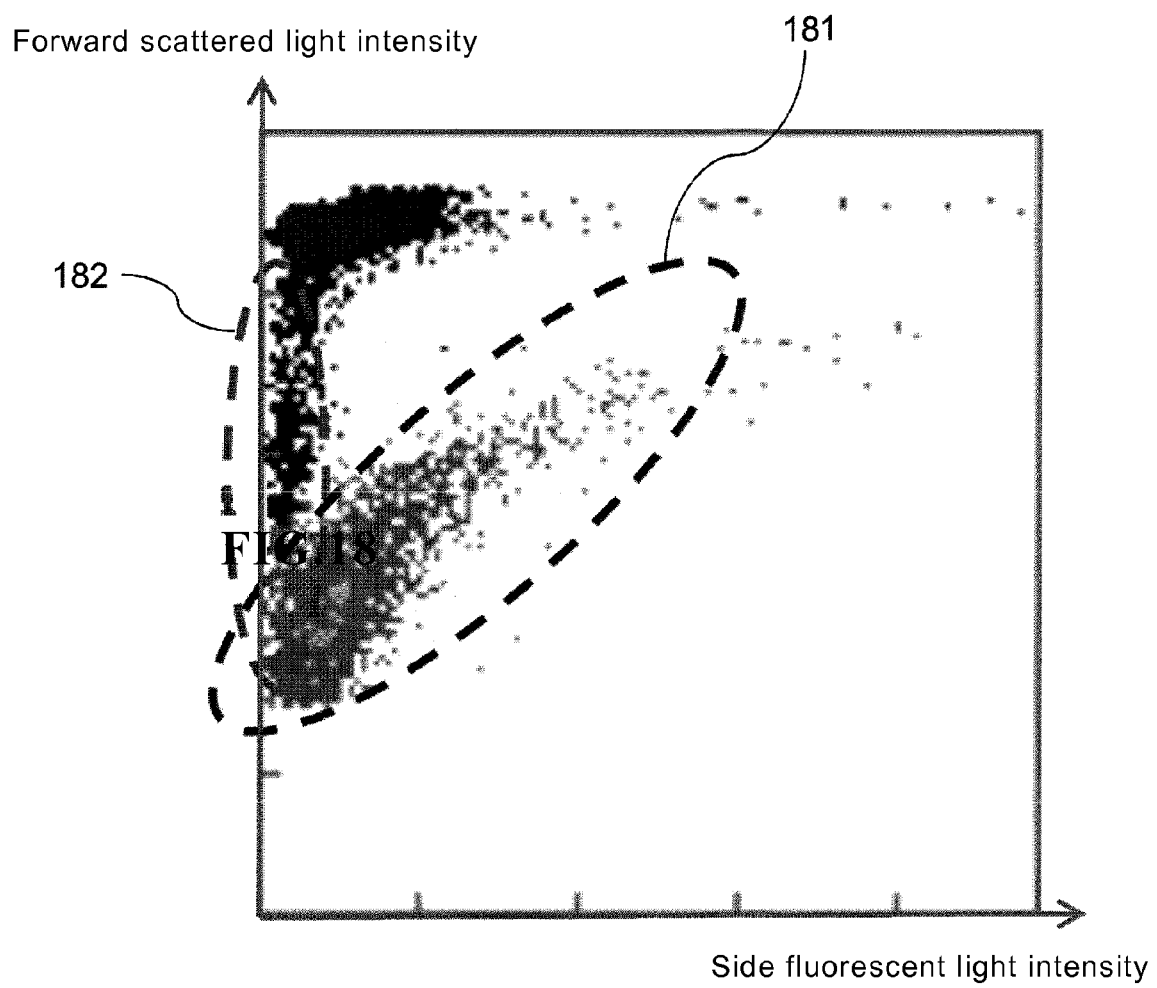
FIG. 18 shows an illustration of a scattergram representing the results of a single PLT measurement by the third measuring device of the second embodiment of the sample analyzer of the present invention.

FIG. 18 shows an example of a scattergram of the first PLT measurement result by the third measuring unit D3 of the second embodiment of the sample analyzer of the present invention. In the scattergram of FIG. 18, the forward scattered light intensity is plotted on the vertical axis and the side fluorescent light intensity is plotted on the horizontal axis. In the example of FIG. 18, there is a region of overlap between the PLT display region 181 and the impurity display region 182, making it difficult to accurately differentiate the regions.

Figure 19:
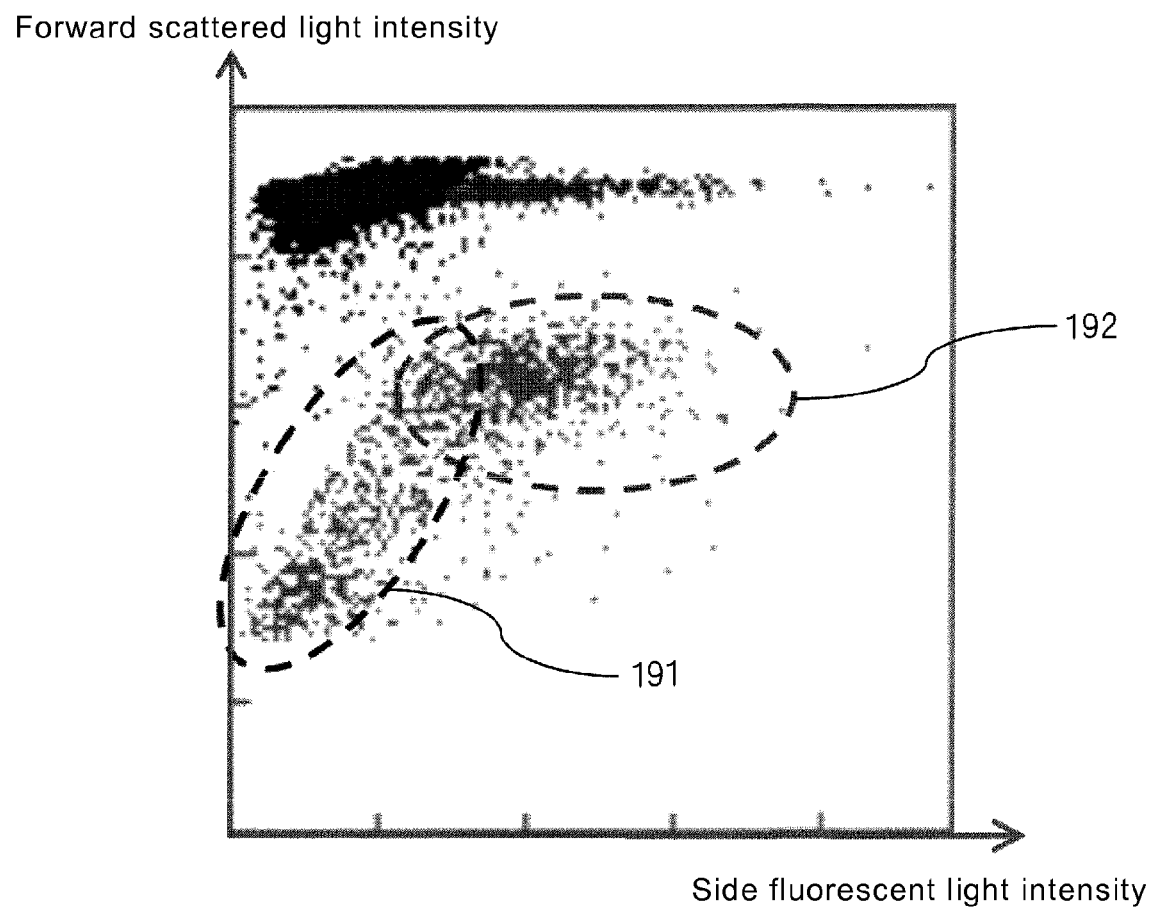
FIG. 19 shows an illustration of a scattergram representing the results of a single PLT measurement by the third measuring device of the second embodiment of the sample analyzer of the present invention.

FIG. 19 shows another example of a scattergram of the first PLT measurement result by the third measuring unit D3 of the second embodiment of the sample analyzer of the present invention. In the scattergram of FIG. 19, the forward scattered light intensity is plotted on the vertical axis and the side fluorescent light intensity is plotted on the horizontal axis. In the example of FIG. 19, there is a region of overlap between the PLT display region 191 and the impurity display region 192, making it difficult to accurately differentiate the regions. The number of occurrences of particles is counted in the predetermined region in which it is difficult to differentiate particles on the scattergrams shown in FIGS. 18 and 19, so that whether a platelet distribution anomaly occurs can be determined according to whether the counted occurrences is greater than a predetermined number.

Returning now to FIG. 17, when the CPU 21 of the operation and display device 2 has determined that a platelet distribution anomaly exists (step S1701: YES), the CPU 21 then determines that the measurement data of the third measuring unit D3 are unreliable (step S1704), and the process continues to step S1705. When the CPU 21 determines that a platelet distribution anomaly does not exist (step S1701: NO), the CPU 21 then determines whether the platelet count is less than a predetermined value based on the measurement data of the third measuring unit D3 (step S1702).

When the CPU 21 has determined that the platelet count value is less than the predetermined value (step S1702: YES), the CPU 21 then determines that the measurement data of the third measuring unit D3 are unreliable (step S1704), and the process continues to step S1705). It is believed that an increase in small platelets may lead to platelets leaked from the count target. When the CPU 21 determines that the platelet count value exceeds the predetermined value (step S1702: NO), the CPU 21 then determines that the measurement data of the third measuring unit D3 are reliable (step S1703), and the process continues to step S1606.

The CPU 21 determines whether a platelet distribution anomaly exists based on the measurement data of the first measuring unit D1 (step S1705).

When the CPU 21 has determined that a platelet distribution anomaly exists (step S1705: YES), the CPU 21 then determines that the measurement data of the first measuring unit D1 are unreliable (step S1708), and the process continues to step S1608). When the CPU 21 determines that a platelet distribution anomaly does not exist (step S1705: NO), the CPU 21 then determines whether the platelet count is less than a predetermined value based on the measurement data of the first measuring unit D1 (step S1706).

When the CPU 21 has determined that the platelet count value is less than the predetermined value (step S1706: YES), the CPU 21 then determines that the measurement data of the first measuring unit D1 are unreliable (step S1708), and the process continues to step S1608). It is believed that an increase in small platelets may lead to platelets leaked from the count target. When the CPU 21 determines that the platelet count value exceeds the predetermined value (step S1706: NO), the CPU 21 then determines that the measurement data of the first measuring unit D1 are reliable (step S1707), and the process continues to step S1607.

Returning now to FIG. 16, when the CPU 21 of the operation and display device 2 has determined that the measurement data of the third measuring unit D3 are unreliable (step S1604: NO), the CPU 21 then determines whether the measurement data of the first measuring unit D1 are reliable (step S1605). The method for determining whether the data are reliable is identical to the method of the first embodiment.

When the CPU 21 has determined that the measurement data of the first measuring unit D1 are unreliable (step S1605: NO), the CPU 21 then transmits an instruction to re-prepare a measurement sample from the same sample to the analyzer body 1 (step S1608). The controller 11 of the analyzer body 1 receives the re-preparation instruction, and issues an instruction to the drive circuit to operate the sample preparing section.

The CPU 21 sends an instruction to re-aspirate the re-prepared measurement sample to the analyzer body 1 (step S1609). The controller 11 of the analyzer body 1 receives the re-aspiration instruction, and issues an instruction to the drive circuit 12 to operate the aspirating tube 14.

The CPU 21 transmits, to the analyzer body 1, a setting change instruction for changing the optical sensitivity so as to be higher than for the first measurement when measuring the re-aspirated measurement sample by the third measuring unit D3, that is, the optical type measuring device (step S1610). The controller 11 of the analyzer body 1 receives the setting change instruction and transmits a setting change signal for changing the optical sensitivity (detection sensitivity) to the third measuring unit D3. Specifically, the CPU 21 transmits an amplification factor which is higher than the amplification factor sent in step S1601 to the amplifiers 324, 334, 344. Thus, the light receiving systems 320, 330, and 340 have higher detection sensitivities than the detection sensitivities in step S1601.

The CPU 21 sends a measurement instruction to measure the re-aspirated measurement sample by the third measuring unit D3, that is, to perform measurement using the optical type measuring device, to the analyzer body 1 (step S1611). The controller 11 of the analyzer body 1 receives the measurement instruction and sends a measurement start signal to the third measuring unit D3.

When the CPU 21 has determined that the measurement data of the third measuring unit D3 are reliable (step S1604: YES), the CPU 21 then uses the measurement data of the third measuring unit D3 as the PLT measurement data (step S1606), and the process ends. When the CPU 21 has determined that the measurement data of the first measuring unit D1 are reliable (step S1605: YES), the CPU 21 then uses the measurement data of the first measuring unit D1 as the PLT measurement data (step S1607), and the process ends.

Figure 20:
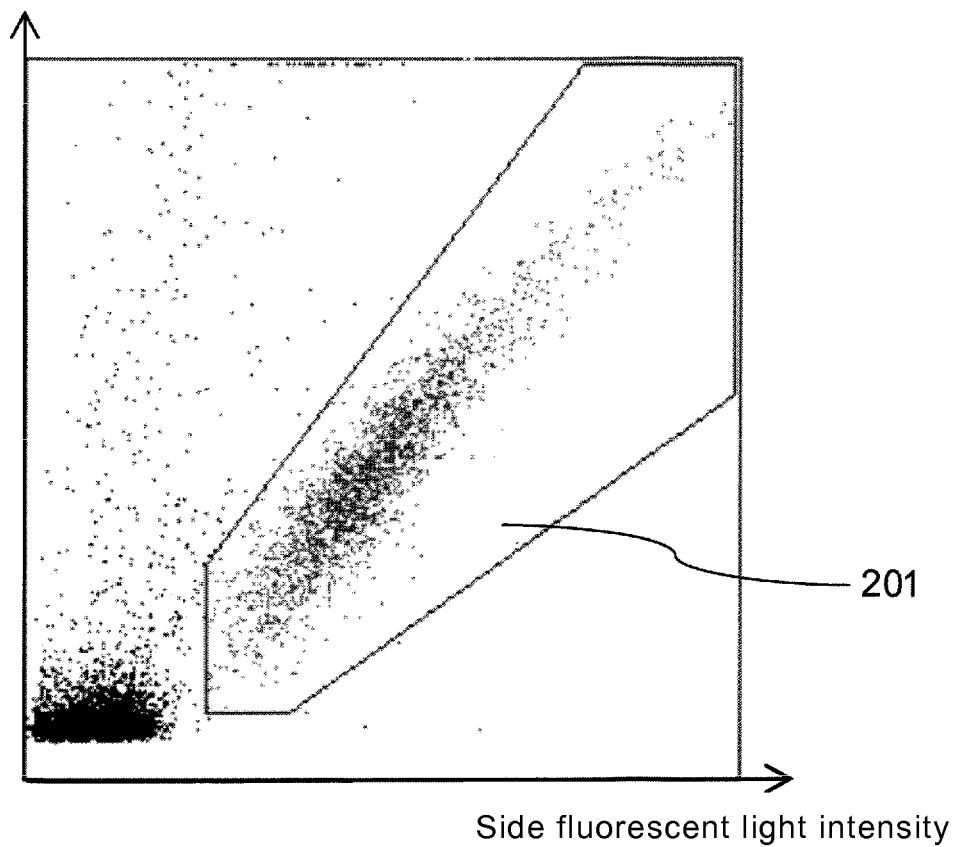
FIG. 20 shows an illustration of a scattergram representing the results of a second PLT measurement by the third measuring device of the second embodiment of the sample analyzer of the present invention.

FIG. 20 shows an example of a scattergram of the second PLT measurement result by the third measuring unit D3 of the second embodiment of the sample analyzer of the present invention. In the scattergram of FIG. 20, the forward scattered light intensity is plotted on the vertical axis and the side fluorescent light intensity is plotted on the horizontal axis. In the example of FIG. 20, relatively small size platelets can be accurately measured by increasing the photosensitivity, and when stain is changed (for example, to Nile Blue) to increase the degree of staining of the platelets, the PLT display region 201 can be better differentiated and displayed. Therefore, blood can be analyzed with greater precision by performing a second measurement by the third measuring unit D3 only when the first detection result is unreliable.

Since the measurement sample is re-prepared based on the same sample, and the operations of the sample preparing section and the aspirating tube 14 are controlled so as to re-aspirate the prepared measurement sample only when reliable measurement data can not be obtained as the detection results of the predetermined components, the reagent used in preparing the sample is conserved, and the increase in the number of measurement processes can be limited to a minimum.

Note that although the first and second embodiments have been described in terms of changing the photosensitivity of the third measuring unit D3 and re-measuring using the third measuring unit D3 as a detection condition, the present invention is not limited to changing the detection condition. For example, the intensity of the irradiating light may also be changed.

Although the first and second embodiments have been described by way of examples of blood analyzers for analyzing blood cells contained in blood using the blood as a sample, the present invention is not limited to this arrangement inasmuch as similar effectiveness can be expected when the present invention is applied to a sample analyzer for analyzing a sample containing bioparticles in urine. Although the analysis results are displayed on the operation and display device 2 in the first and second embodiments, the present invention is not particularly limited to this arrangement inasmuch as the analysis results may also be displayed on the display device of another computer connected over a network.

Although the first and second embodiments employ an electrical resistance type detector as the first measuring unit D1 and employ an optical type detector as the third measuring unit D3, the present invention is not limited to this arrangement inasmuch as an optical type detector may be used as the first measuring unit D1 and an electrical resistance type detector may be used as the third measuring unit D3, or at least one of the first measuring unit D1 and third measuring unit D3 may be a combination detector which combines optical type and electrical resistance type detection.

Although the photosensitivity (first detection condition) used in the third measuring unit D3 in step S1601 is a photosensitivity for detecting platelets and red blood cells, and the photosensitivity (second detection condition) used in the third measuring unit D3 in step S1611 is a photosensitivity for detecting only platelets in the second embodiment, the present invention is not limited to this arrangement inasmuch as the first detection condition may be changed to a photosensitivity for detecting reticulocytes, platelets, and red blood cells, and the second detection condition may be changed to a photosensitivity for detecting platelets and red blood cells. Note that in order to obtain a highly reliable measurement result, the type of component to be detected would preferably utilize the first detection condition more often than the second detection condition.

Although the first and second embodiments are described in terms of a blood analyzer in which blood within a single collection tube 3 is placed at a predetermined position within the analyzer body 1, it is to be understood that similar effectiveness is attained in the case of a sample analyzer that performs desired measurements of blood by moving a rack holding a plurality of collection tubes 3 via a conveyor mechanism. In this case, when blood must be remeasured due to unreliable measurement data, an instruction for moving the corresponding collection tube 3 must be sent to the controller of the conveyor mechanism so as to retransport the corresponding collection tube 3 to the position of the aspirating tube 14. Of course, when the aspirating tube 14 is a movable type, an instruction may also be issued to move the position of the aspirating tube 14 to the position of the corresponding collection tube 3.

What is claimed is:

1. A sample analyzer comprising:
   a sample preparing section comprising one or more chambers to prepare a measurement sample by mixing a part of a blood sample and a reagent therein;
   a first detector configured to detect electronic resistance of the measurement sample so as to detect platelets;
   a second detector comprising: a flow cell through which the measurement sample flows: a light emitting unit for irradiating light; and a light receiving unit for receiving light from the light emitting unit, so as to optically detect platelets; and
   a controller configured to perform operations, comprising:
   (a) controlling the sample preparing section to prepare a first measurement sample by mixing a first part of a blood sample and a first reagent, provide the first measurement sample to the first detector, prepare a second measurement sample by mixing a second part of the blood sample and a second reagent, and provide the second measurement sample to the second detector;
   (b) obtaining a first result, detected by the first detector, regarding platelets in the first measurement sample, and obtaining a second result, detected by the second detector, regarding platelets in the second measurement sample;
   (c) determining reliability of the first result and the second result;
   (d) when the first and second results have been determined to be unreliable, controlling the second detector to change a detection sensitivity of the light receiving unit;
   (e) controlling the sample preparing section to prepare a third measurement sample by using a third part of the blood sample, and provide the third measurement sample to the second detector; and
   (f) obtaining a third result, detected by the second detector, regarding platelets in the third measurement sample.

2. The sample analyzer according to claim 1, wherein the second detector detects light scattering of the second measurement sample.

3. The sample analyzer according to claim 1, wherein the light receiving unit comprises a detecting part for detecting light and for outputting signal corresponding to an amount of detected light, and an amplifier for amplifying the signal output from the detecting part; and the detection sensitivity relates to the level of amplification by the amplifier.

4. The sample analyzer according to claim 1, wherein the third reagent has different composition from the second reagent.

5. The sample analyzer according to claim 1, wherein
   the controller is configured to obtain a platelet count value by the first measurement as the first result and
   a frequency distribution of platelets by the second measurement as the second result.

6. The sample analyzer according to claim 5, wherein
   in step (d), the controller determines the first result is unreliable when the platelet count value is less than the predetermined value, and the second result is unreliable when the frequency distribution of platelets is abnormal.

* * * * *